US009372153B2

(12) United States Patent
Nishino et al.

(10) Patent No.: US 9,372,153 B2
(45) Date of Patent: Jun. 21, 2016

(54) DRYNESS FRACTION DISTRIBUTION MEASURING DEVICE AND DRYNESS FRACTION DISTRIBUTION MEASURING METHOD

(71) Applicant: Azbil Corporation, Tokyo (JP)

(72) Inventors: Giichi Nishino, Tokyo (JP); Yasuhiro Goshoo, Tokyo (JP); Shiko Tanabe, Tokyo (JP)

(73) Assignee: AZBIL CORPORATION, Tokyo (JP)

( * ) Notice: Subject to any disclaimer, the term of this patent is extended or adjusted under 35 U.S.C. 154(b) by 0 days.

(21) Appl. No.: 14/760,225

(22) PCT Filed: Dec. 25, 2013

(86) PCT No.: PCT/JP2013/084574
§ 371 (c)(1),
(2) Date: Jul. 10, 2015

(87) PCT Pub. No.: WO2014/109228
PCT Pub. Date: Jul. 17, 2014

(65) Prior Publication Data
US 2015/0362426 A1 Dec. 17, 2015

(30) Foreign Application Priority Data
Jan. 10, 2013 (JP) .................................. 2013-002536

(51) Int. Cl.
*G01N 21/3554* (2014.01)
(52) U.S. Cl.
CPC ...... *G01N 21/3554* (2013.01); *G01N 2201/062* (2013.01)
(58) Field of Classification Search
CPC .......................... G01N 21/3554; G01N 21/00
USPC ....................................................... 356/437
See application file for complete search history.

(56) References Cited

U.S. PATENT DOCUMENTS

| 8,610,894 B2 * | 12/2013 | Nishino | ............... | G01N 21/314 |
| | | | | 356/320 |
| 2010/0000111 A1 | 1/2010 | Takeuchi | | |
| 2012/0147375 A1* | 6/2012 | Nishino | ............... | G01N 21/314 |
| | | | | 356/437 |

FOREIGN PATENT DOCUMENTS

| JP | H08-312908 A | 11/1996 |
| JP | 2005-091006 A | 4/2005 |

(Continued)

OTHER PUBLICATIONS

International Search Report dated Mar. 25, 2014 which issued during the prosecution of International Application No. PCT/JP2013/084574, which corresponds to the present application.

Primary Examiner — Roy M Punnoose
(74) Attorney, Agent, or Firm — Troutman Sanders LLP

(57) ABSTRACT

A dryness fraction distribution measuring device, includes: a light-emitting body that illuminates a gas/liquid two-phase flow with light; an environment sensor that measures at least one of temperature or pressure in a gas/liquid two-phase flow; a plurality of photodetecting elements that receive respective lights that have traversed moist steam; a relationship storing portion that stores, for each temperature or pressure, a relationship between an intensity of light that has traversed the gas/liquid two-phase flow and a dryness fraction of the gas/liquid two-phase flow; and a dryness fraction identifying portion that identifies a dryness fraction of the gas/liquid two-phase flow for each position corresponding to the plurality of photodetecting elements, based on the relationships between the measured values for the detected light intensities of the lights detected by the respective photodetecting elements and the values for the temperatures and pressures measured by the environment sensor.

18 Claims, 30 Drawing Sheets

(56) References Cited

FOREIGN PATENT DOCUMENTS

| JP | 2005-156438 A | 6/2005 |
| JP | 2011-117869 A | 6/2011 |
| JP | 2012-122961 A | 6/2012 |
| WO | 2007/063840 A1 | 6/2007 |

* cited by examiner

Wavy Flow
21

Bubble Flow

21

Slug Flow
21

Laminar Flow
21

Dispersed Annular Flow — 21

FIG. 21

Intensity of Detected Light at Respective
Measurement Positions
(Arbitrary Units)

| Position in Perpendicular Direction \ Position in Direction of Flow | 1 | 2 | 3 | 4 | 5 |
|---|---|---|---|---|---|
| 1 | 12 | 15 | 18 | 12 | 8 |
| 2 | 10 | 13 | 16 | 9 | 6 |
| 3 | 5 | 10 | 8 | 4 | 3 |
| 4 | 3 | 7 | 4 | 2 | 1 |
| 5 | 3 | 6 | 3 | 1 | 1 |

FIG. 25

Intensity of Detected Light at Respective
Measurement Positions
(Arbitrary Units)

| Position in Perpendicular Direction \ Position in Direction of Flow | 1 | 2 | 3 | 4 | 5 |
|---|---|---|---|---|---|
| 1 | 3 | 5 | 3 | 4 | 3 |
| 2 | 1 | 1 | 1 | 1 | 1 |
| 3 | 1 | 1 | 1 | 1 | 1 |
| 4 | 1 | 1 | 1 | 1 | 1 |
| 5 | 3 | 4 | 3 | 4 | 3 |

DRYNESS FRACTION DISTRIBUTION MEASURING DEVICE AND DRYNESS FRACTION DISTRIBUTION MEASURING METHOD

CROSS-REFERENCE TO RELATED APPLICATIONS

This is a U.S. national phase application under 35 U.S.C. §371 of International Patent Application No. PCT/JP2013/084574, filed on Dec. 25, 2013, and claims benefit of priority to Japanese Patent Application No. JP 2013-002536, filed on Jan. 10, 2013. The International Application was published on Jul. 17, 2014, as International Publication No. WO 2014/109228 under PCT Article 21(2). The entire contents of these applications are hereby incorporated by reference.

FIELD OF TECHNOLOGY

The present disclosure relates to a measuring technology, relating to a dryness fraction distribution measuring device and dryness fraction distribution measuring method.

BACKGROUND

After water reaches its boiling point, it becomes moist steam that is a mixture of water vapor gas (the gas phase part) and water droplets (the liquid phase part). Here the weight ratio of the water vapor gas relative to the moist steam is termed the "dryness fraction." For example, if water vapor gas and water droplets exist at half each, then the dryness fraction would be 0.5. Moreover, when there are no water droplets but instead there is only water vapor gas, then the dryness fraction would be 1.0. From the perspective of efficiency of use of the apparent heat and latent heat within the moist steam in heat exchanging equipment, and the like, from the perspective of preventing corrosion of turbine blades in steam turbines, and so forth, it is desirable that the dryness fraction of the moist steam be brought to near 1.0. Because of this, a variety of methods have been proposed whereby to measure the moist steam. For example, Japanese Unexamined Patent Application Publication H8-312908 (the JP '908) discloses a technology for calculating the dryness fraction by calculating the saturated hydraulic enthalpy and the saturated steam enthalpy using a saturated steam table based on the dry steam flow rates and pressures before and after a pressure regulating valve, taking advantage of the fact that there is no change in total enthalpy across a pressure regulating valve that is disposed in a pipe.

However, in the technology disclosed in the JP '908, it is necessary to cause the moist steam that is to be measured to undergo a state change from the two-phase state to the gas phase state, and also necessary to stabilize, in the gas phase state, that which is to be measured, and thus there is a problem in that measuring the dryness fraction is time-consuming. Moreover, the technology disclosed in the JP '908 is unable to measure the distribution of the dryness fraction within the moist steam.

Given this, one aspect of the present disclosure is the provision of a dryness fraction distribution measuring device and dryness fraction distribution measuring method whereby the dryness fraction distribution can be measured accurately and easily.

SUMMARY

A form of the present disclosure is summarized as being a dryness fraction distribution measuring device including: a light-emitting body that irradiates gas/liquid two-phase flow; a plurality of photodetecting elements wherein each receives light that passes through the gas/liquid two-phase flow; and a dryness fraction identifying portion that identifies dryness of the gas/liquid two-phase flow, positioned facing each of the plurality of photodetecting elements, based on the intensity of light detected by each of the plurality of photodetecting elements.

A form of the present disclosure is summarized as being a dryness fraction distribution measuring method including: irradiating gas/liquid two-phase flow; each of a plurality of photodetecting elements each receiving light that passes through the gas/liquid two-phase flow; and identifying dryness of the gas/liquid two-phase flow, positioned facing each of the plurality of photodetecting elements, based on the intensity of light detected by each of the plurality of photodetecting elements.

The present disclosure enables the provision of a dryness fraction distribution measuring device and dryness fraction distribution measuring method whereby the dryness fraction distribution can be measured accurately and easily.

BRIEF DESCRIPTIONS OF THE DRAWINGS

FIG. 21 is a table of the light reception intensities in respective measurement locations in the Example according to the present invention.

FIG. 25 is a table of the light reception intensities in respective measurement locations in the Example according to the present invention.

DETAILED DESCRIPTION

Examples of the present invention will be described below. In the descriptions of the drawings below, identical or similar components are indicated by identical or similar codes. Note that the diagrams are schematic. Consequently, specific measurements should be evaluated in light of the descriptions below. Furthermore, even within these drawings there may, of course, be portions having differing dimensional relationships and proportions.

Example

Figure 1:
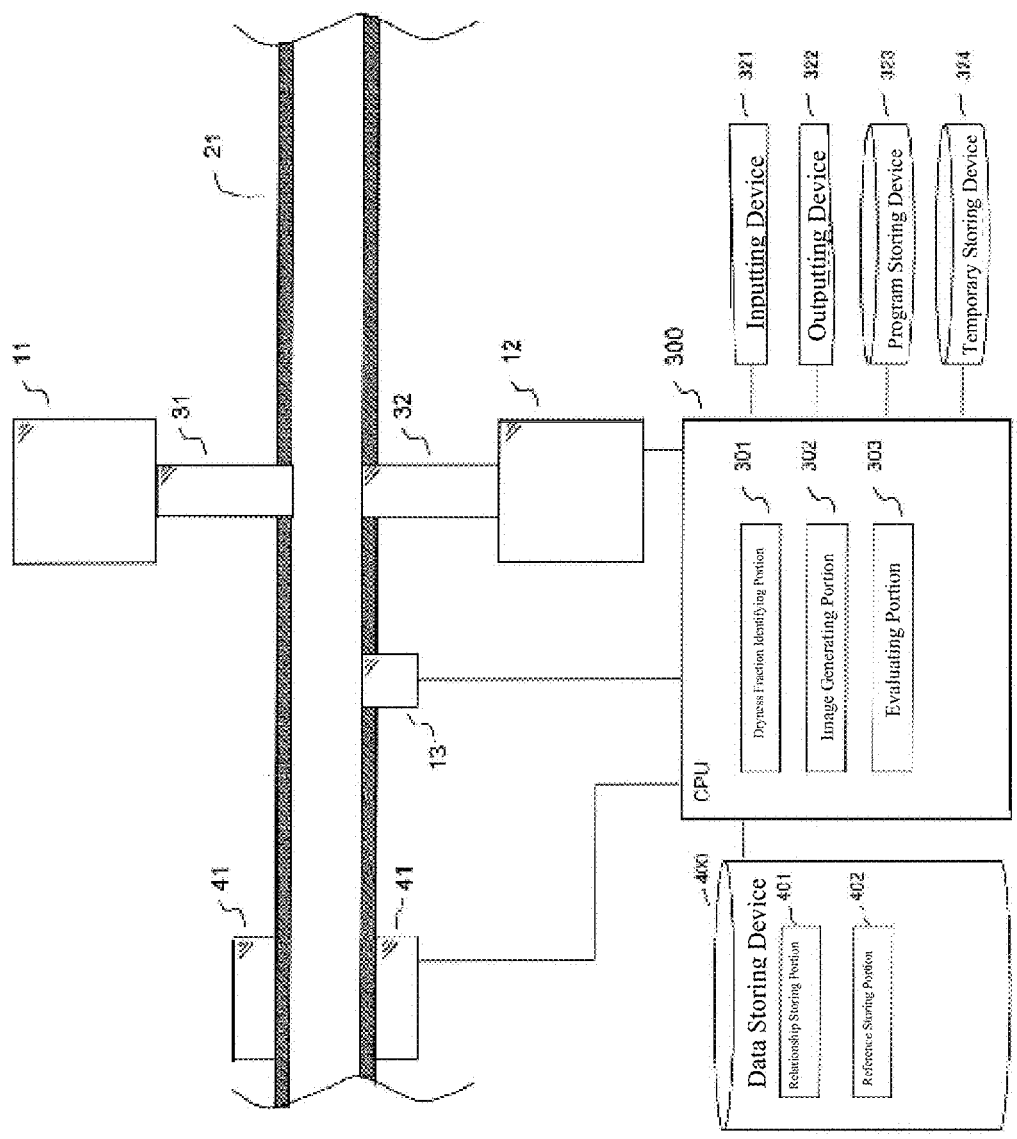
FIG. 1 is a schematic diagram of a dryness fraction distribution measuring device as set forth in Example according to the present disclosure.

A dryness fraction distribution measuring device according to Example according to the present invention, as illustrated in FIG. 1, includes: a light-emitting body 11 for irradiating gas/liquid two-phase flow that is to be measured; a photodetecting body 12 that includes a plurality of photodetecting elements wherein each receives light that passes through the gas/liquid two-phase flow that is being measured; and a dryness fraction identifying portion 301 for identifying dryness of the gas/liquid two-phase flow at positions facing each of the plurality of photodetecting elements, based on the intensity of light detected by each of the plurality of photodetecting elements. Here the intensity of light may refer to the intensity of light detected by the photodetecting body 12, or may refer to the amount of light absorbed by the gas/liquid two-phase flow. The gas/liquid two-phase flow that is to be measured flows within a pipe 21.

Figure 2:
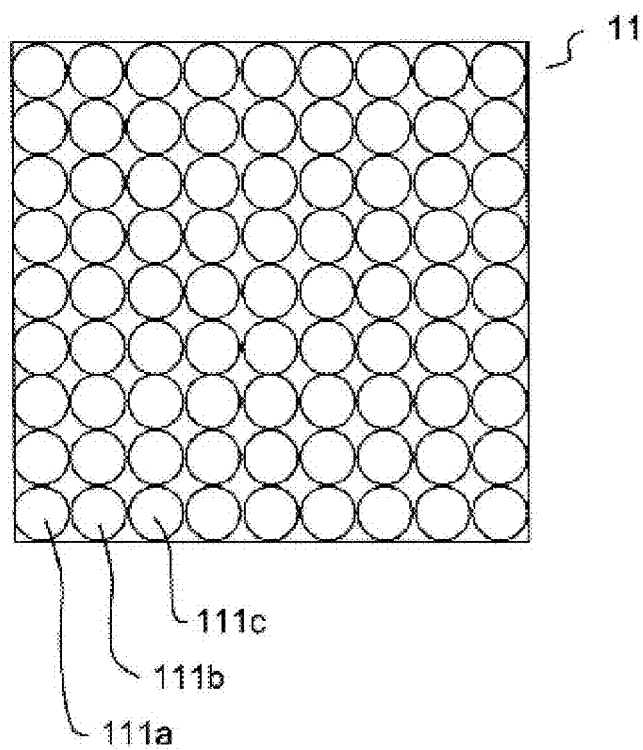
FIG. 2 is a front view of a light-emitting body according to the Example according to the present invention.
Figure 3:
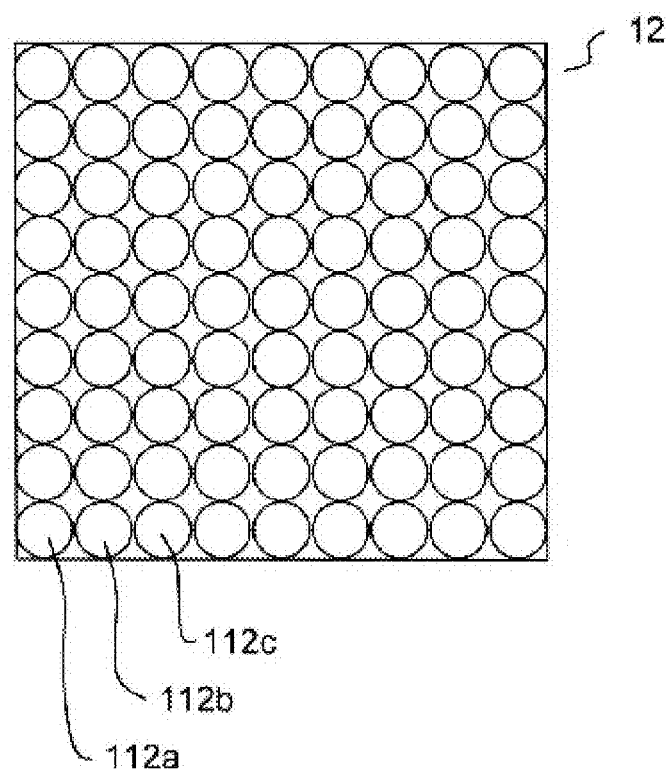
FIG. 3 is a front view of a photodetecting body according to the Example according to the present invention.

The light-emitting body 11 may be a planar light-emitting body, or, as illustrated in FIG. 2, may include a plurality of light-emitting elements 111a, 111b, 111c, and so forth, that are disposed in the form of a grid. Light-emitting diodes, super-luminescent diodes, semiconductor lasers, laser oscillators, and the like, can be used as the plurality of light-emitting elements 111a, 111b, 111c, and so forth. Moreover, as illustrated in FIG. 3, a plurality of photodetecting elements 112a, 112b, 112c, and so forth, is arranged in a two-dimensional grid, facing the pipe 21. Each of the plurality of photodetecting elements 112a, 112b, 112c, and so forth, can use an optical intensity detecting element such as a photodiode.

The arrangement of the plurality of light-emitting elements 111a, 111b, 111c, and so forth, illustrated in FIG. 2, and the arrangement of the plurality of photodetecting elements 112a, 112b, 112c, and so forth, illustrated in FIG. 3, have a one-to-one correspondence, making it possible to suppress the non-uniformity in intensities that derives from differences in optical path lengths for the lights that are detected by the individual photodetecting elements 112a, 112b, 112c, and so forth.

Moreover, the dryness fraction distribution measuring device according to the Example, as illustrated in FIG. 1, further includes an environment sensor 13 for measuring the temperature and/or pressure of the gas/liquid two-phase flow that is subject to measurement, and a relationship storing portion 401 for storing, for each temperature or pressure, a relationship between the intensity of light passing through the gas/liquid two-phase flow and the dryness fraction of the gas/liquid two-phase flow, established in advance. The dryness fraction identifying portion 301 identifies the values for the gas/liquid two-phase flow dryness factors at positions corresponding to each of the plurality of photodetecting elements based on the measured values for the intensities of light, by the photodetecting body 12, the measured values for the temperatures or pressures by the environment sensor 13, and the relationships that are stored in the relationship storing portion 401.

Figure 4:
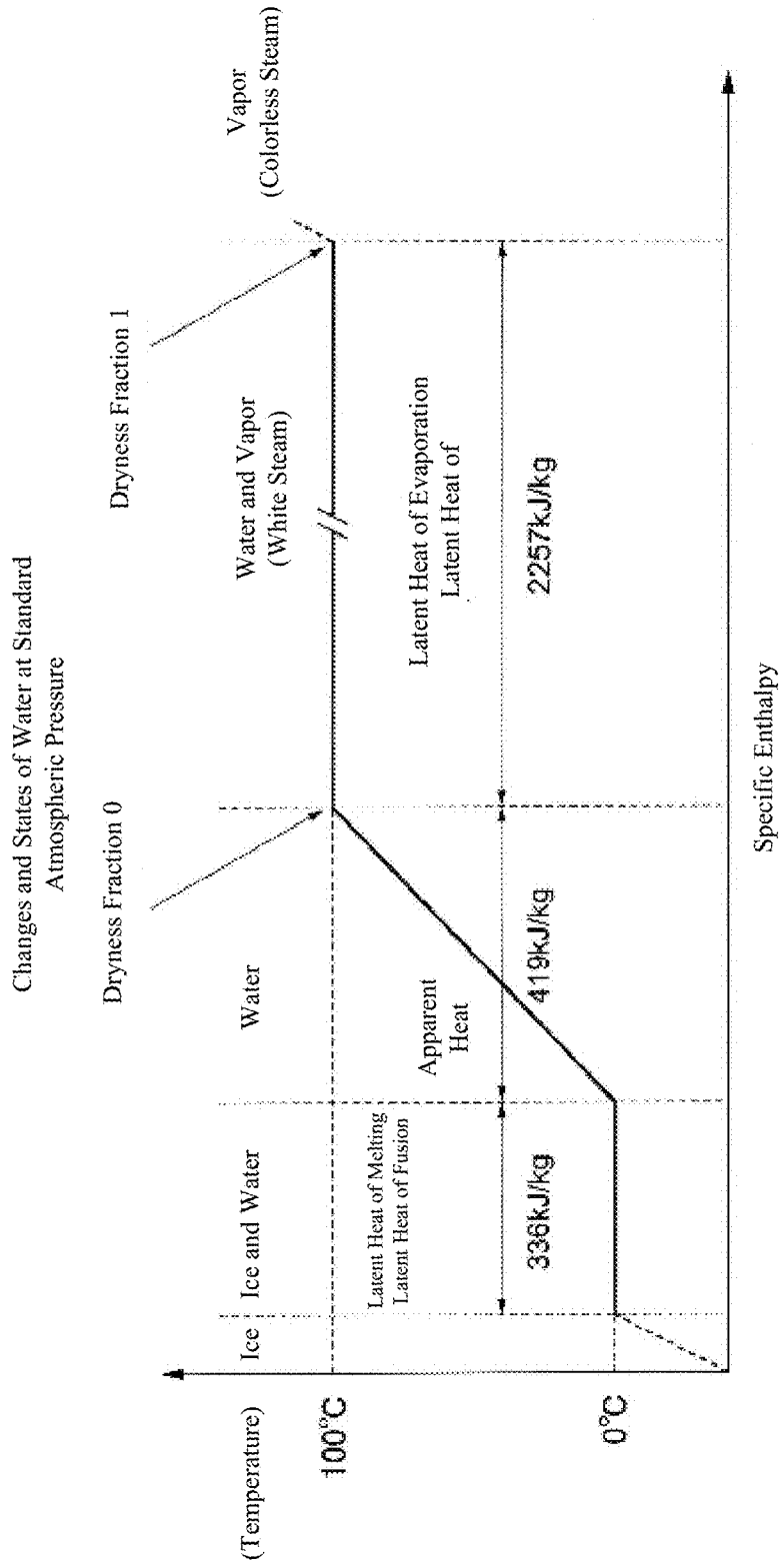
FIG. 4 is a graph illustrating a state change in moisture at atmospheric pressure in the Example according to the present disclosure.

As illustrated in FIG. 4, under standard atmospheric pressure, after water reaches its boiling point (100° C.), it becomes a gas/liquid two-phase flow (moist steam) wherein water, as liquid droplets, and steam are mixed to be in a coexisting state. Here the specific gravity of the vapor gas relative to the total weight of the moist steam is termed the "dryness fraction." Consequently, saturated vapor has a dryness fraction of 1, and saturated liquid has a dryness fraction of 0. Conversely, the dryness fraction is also defined as the ratio of the difference between the moist steam specific enthalpy and the saturated liquid specific enthalpy, relative to the latent heat specific enthalpy.

Figure 5:
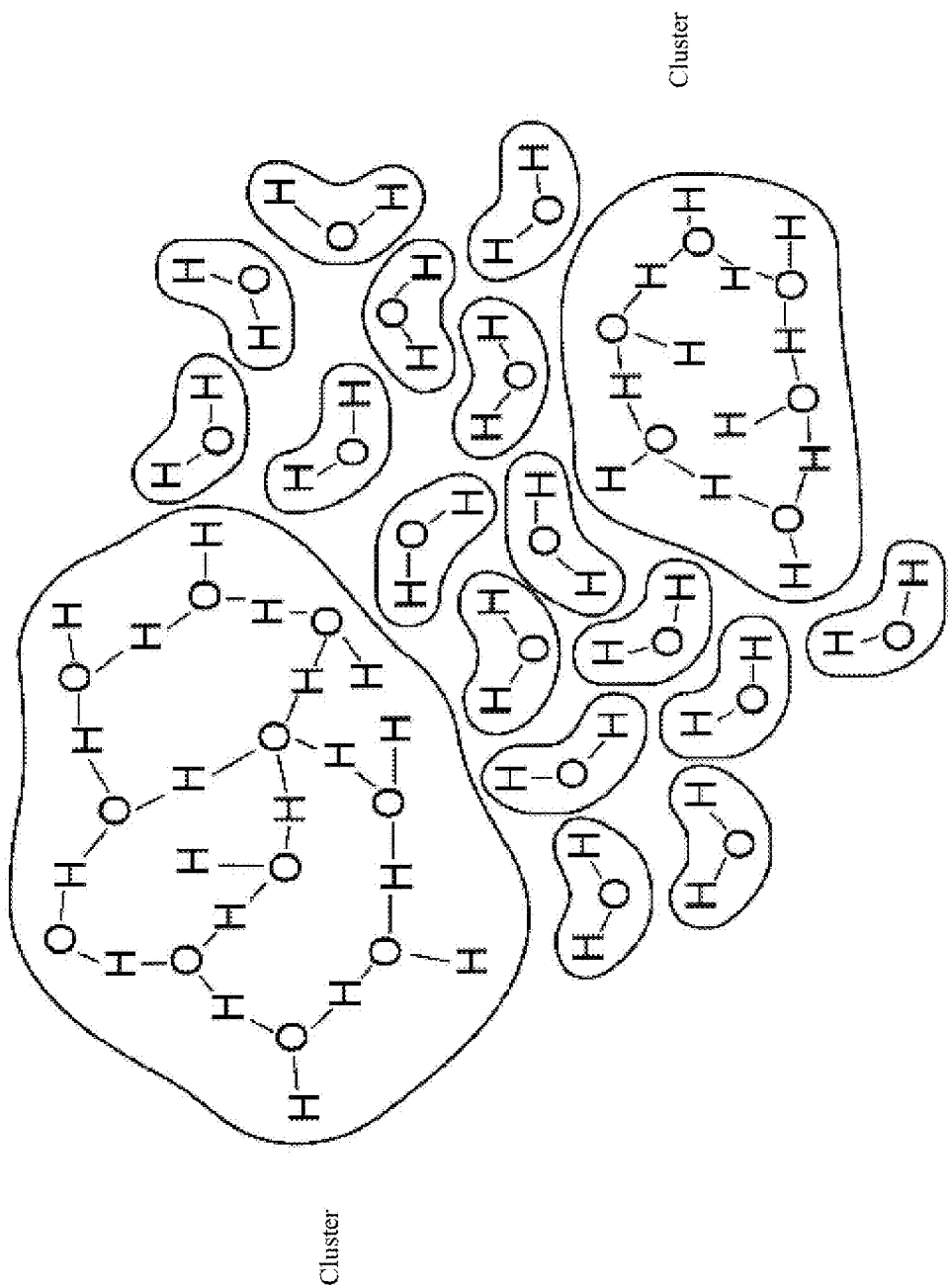
FIG. 5 is a schematic diagram of a cluster of water molecules according to the Example according to the present invention.
Figure 6:
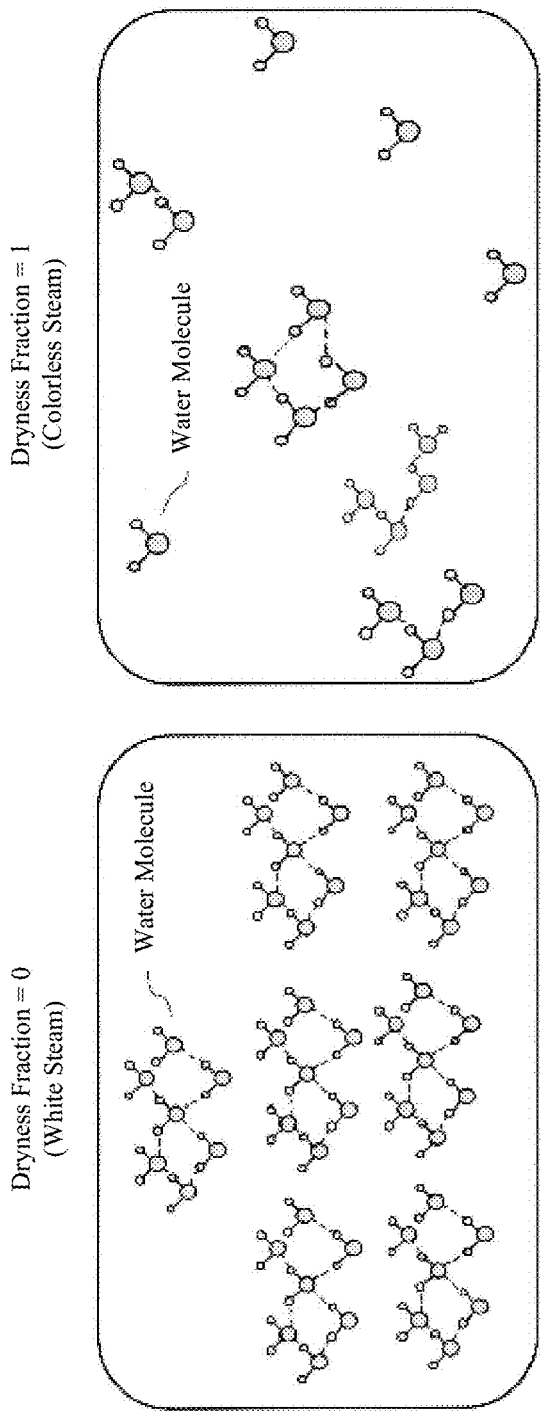
FIG. 6 is a schematic diagram illustrating the state of a water molecule depending on the dryness fraction according to the Example according to the present disclosure.
Figure 7:
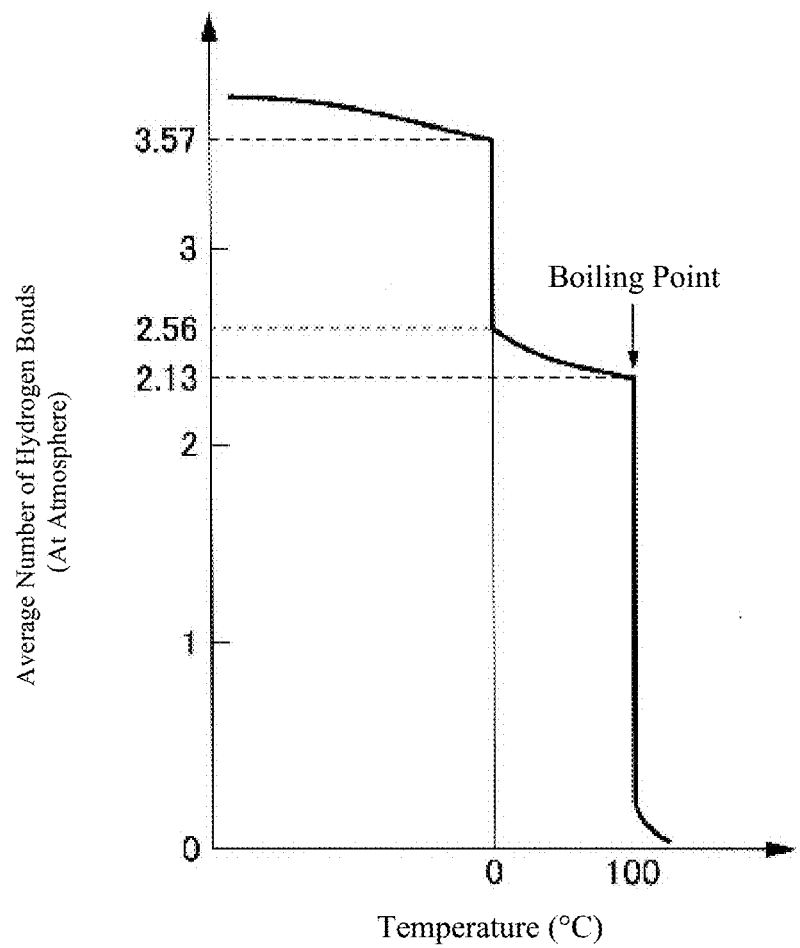
FIG. 7 is a graph illustrating an example of the relationship between temperature and the average hydrogen bond count of a cluster of water molecules in the Example according to the present disclosure.

Water undergoes phase changes through differences in the numbers of hydrogen bonds that are formed between the water molecules. In the moist steam, the water molecules bond together through hydrogen bonds to form clusters as illustrated in FIG. 5. As illustrated in FIG. 6 and FIG. 7, the average number of hydrogen bonds in a cluster in moist steam with a dryness fraction of 0 at atmospheric pressure is, for example, 2.13. The average number of hydrogen bonds in a cluster falls as the dryness fraction approaches 1, where there tends to be an increase in the water molecules that exist singly.

Figure 8:
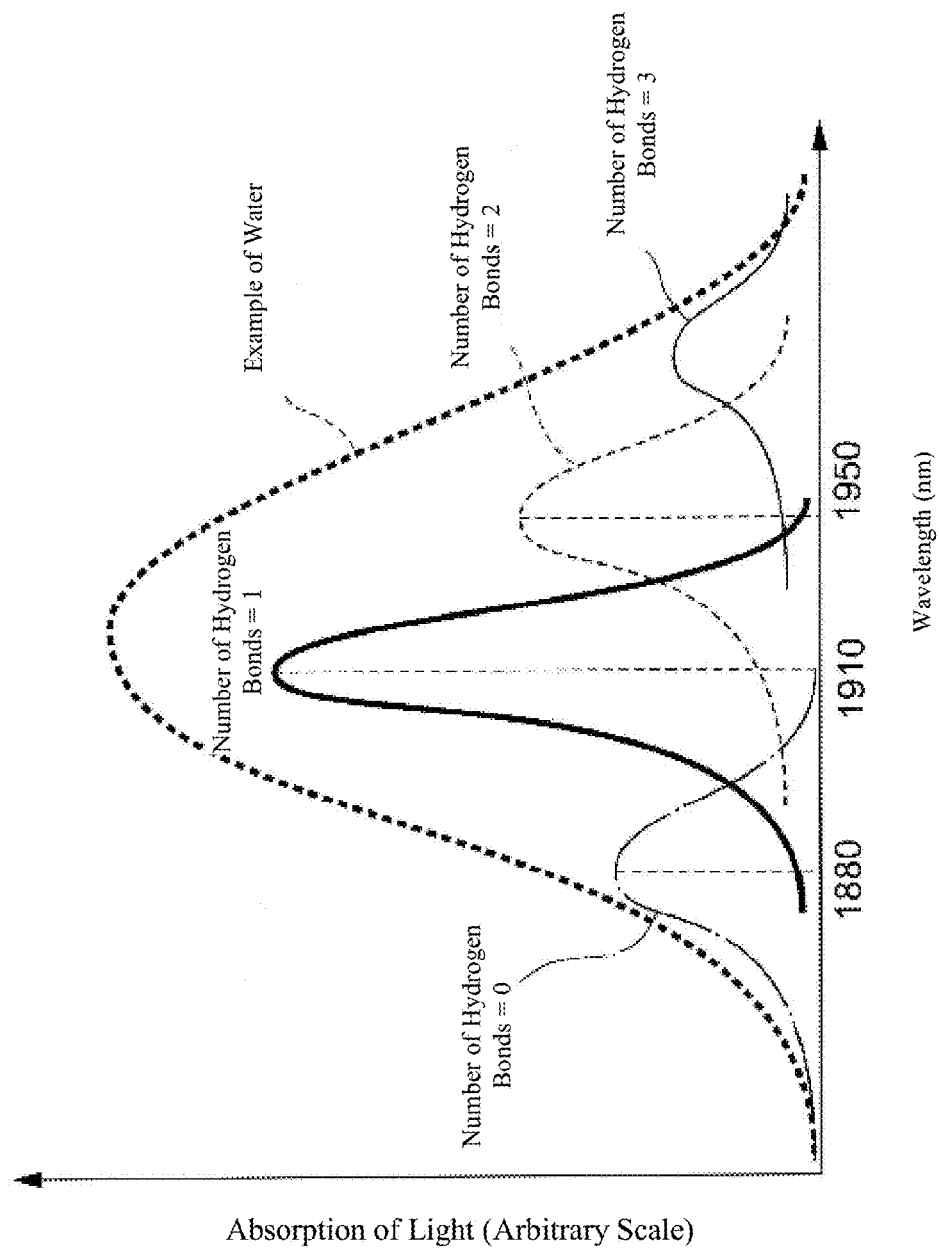
FIG. 8 is a graph illustrating an example of the water molecule absorption spectrum according to the Example according to the present disclosure.
Figure 9:
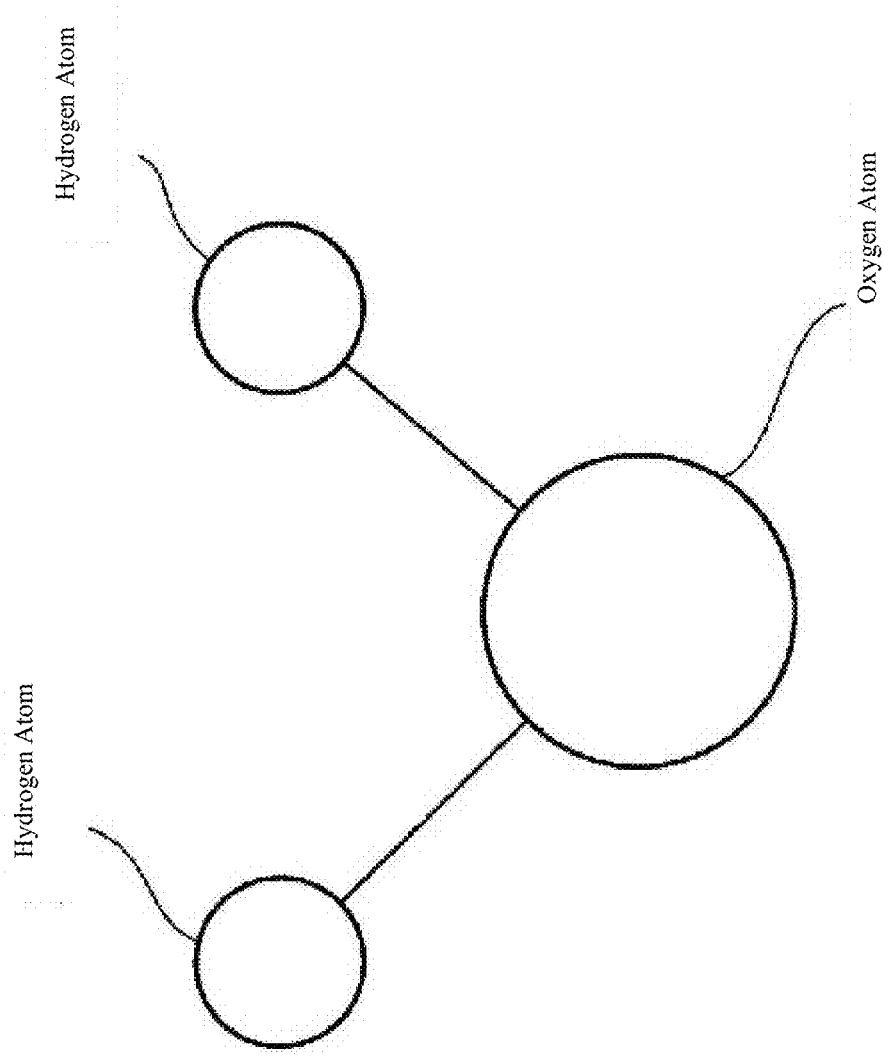
FIG. 9 is a schematic diagram of a water molecule that exists singly according to the Example according to the present disclosure.
Figure 10:
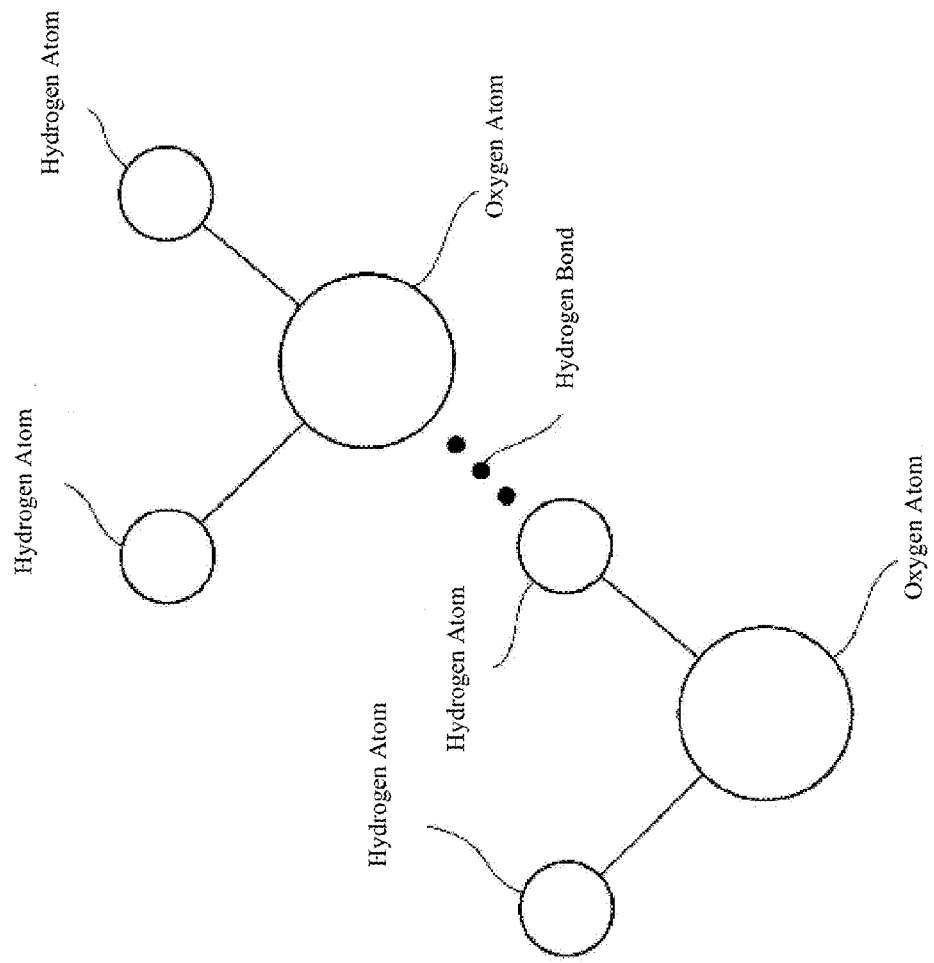
FIG. 10 is a schematic diagram of a two water molecules that are bonded by a single hydrogen bond according to the Example according to the present disclosure.
Figure 11:
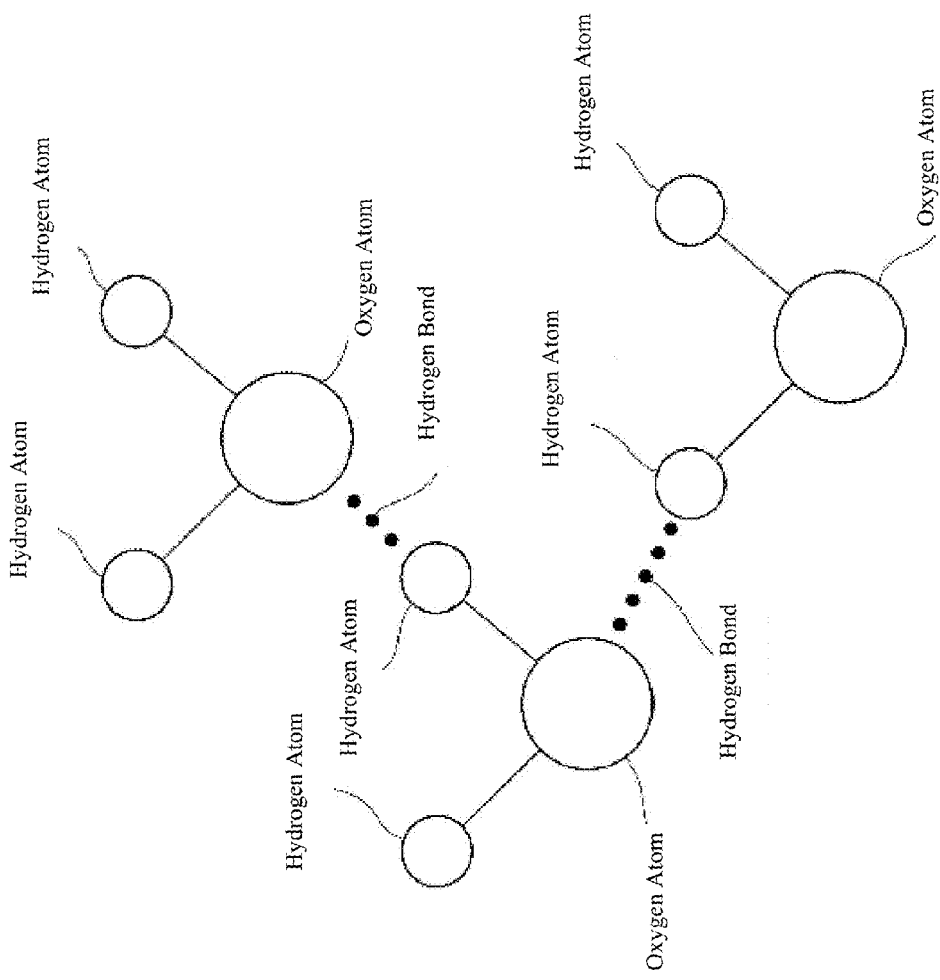
FIG. 11 is a schematic diagram of a three water molecules that are bonded by a double hydrogen bond according to the Example according to the present disclosure.

FIG. 8 is an example of an exertion spectrum exhibited by water molecules. As illustrated in FIG. 9, the water molecules that exist singly provide an absorption spectrum that has peaks at 1840 and 1880 nm. As illustrated in FIG. 10, the water molecules wherein two water molecules are bonded by a single hydrogen bond provide an absorption spectrum that has a peak at 1910 nm. As illustrated in FIG. 11, the water molecules wherein three water molecules are bonded by a two hydrogen bonds provide an absorption spectrum that has a peak at 1950 nm. In general, the greater the number of hydrogen bonds included in a cluster formed by water molecules the longer the wavelength of the peak of the absorption spectrum.

In FIG. 1, the dryness fraction distribution measuring device is connected to a pipe 21 through which moist steam passes. The light-emitting body 11 produces light having a single wavelength. For example, the wavelength of light that is produced by the light-emitting body 11 is set so as to be correlated to the number of hydrogen bonds that are formed between the water molecules in the cluster. For example, the wavelength of the light that is emitted by the light-emitting body 11 may be the 1880 nm wherein the absorption peak for water molecules appears when the number of hydrogen bonds is zero, or maybe the 1910 nm wherein the absorption peak of water molecules appears when the number of hydrogen bonds is 1. Note that insofar as the wavelength of the light that is emitted by the light emitting body 11 is within the band of wavelength that is absorbed by water, it may be at a wavelength other than a peak wavelength for absorption by water molecules. For example, the wavelength of the light that is emitted by the light-emitting body 11 may be between 1180 and 1910 nm.

An optical waveguide 31 is connected to the light-emitting body 11. The optical waveguide 31 carries the light that is produced by the light-emitting body 11 into a pipe 21. For example, the optical waveguide 31 passes through a side wall of the pipe 21. Conversely, an optically transparent window may be provided in the side wall of the pipe 21, and the optical waveguide 31 may be connected to the window. The light that is carried by the optical waveguide 31 enters into the pipe 21 from the end portion of the optical waveguide 31. While plastic optical fibers made out of poly methyl methacrylate (PMMA), glass optical fibers made out of quartz glass, or the like, may be used in the optical waveguide 31, there is no limitation thereto insofar as it is capable of carrying the light that is produced by the light-emitting body 11.

If the light-emitting body 11 emits, for example, light with a wavelength of 1880 nm, then the light with the wavelength of 1880 nm will, within the pipe 21, be absorbed by the water molecules that exist singly that are included in the moist steam. As described above, the average number of hydrogen bonds there are within the water molecule cluster falls as the dryness fraction goes from 0 to 1. Consequently, there is a tendency for the light with the wavelength of 1880 nm to be absorbed more greatly as the dryness fraction of the moist steam within the pipe 21 goes from 0 to 1.

Conversely, if the light-emitting body 11 emits, for example, light with a wavelength of 1910 nm, then the light with the wavelength of 1910 nm will, within the pipe 21, be absorbed by the two-molecule water molecules that have single hydrogen bonds, which are included in the moist steam. There is a tendency for the light with the wavelength of 1910 nm to be absorbed less greatly as the dryness fraction of the moist steam within the pipe 21 goes from 0 to 1.

An optical waveguide 32 into which enters light that has traversed the pipe 21 is connected to the pipe 21. The optical waveguide 32 guides, to the photodetecting body 12, the light that has traversed the moist steam within the pipe 21. An end portion of the optical waveguide 32 faces an end portion of the optical waveguide 31. Moreover, the optical waveguide 32 passes through a side wall of the pipe 21. Conversely, an optically transparent window may be provided in the side wall of the pipe 21, and the optical waveguide 32 may be connected to the window.

Note that the light-emitting body 11 may be disposed in the side wall of the pipe 21 to eliminate the optical waveguide 31. Moreover that the photodetecting body 12 may be disposed in the side wall of the pipe 21 to eliminate the optical waveguide 32.

Figure 12:
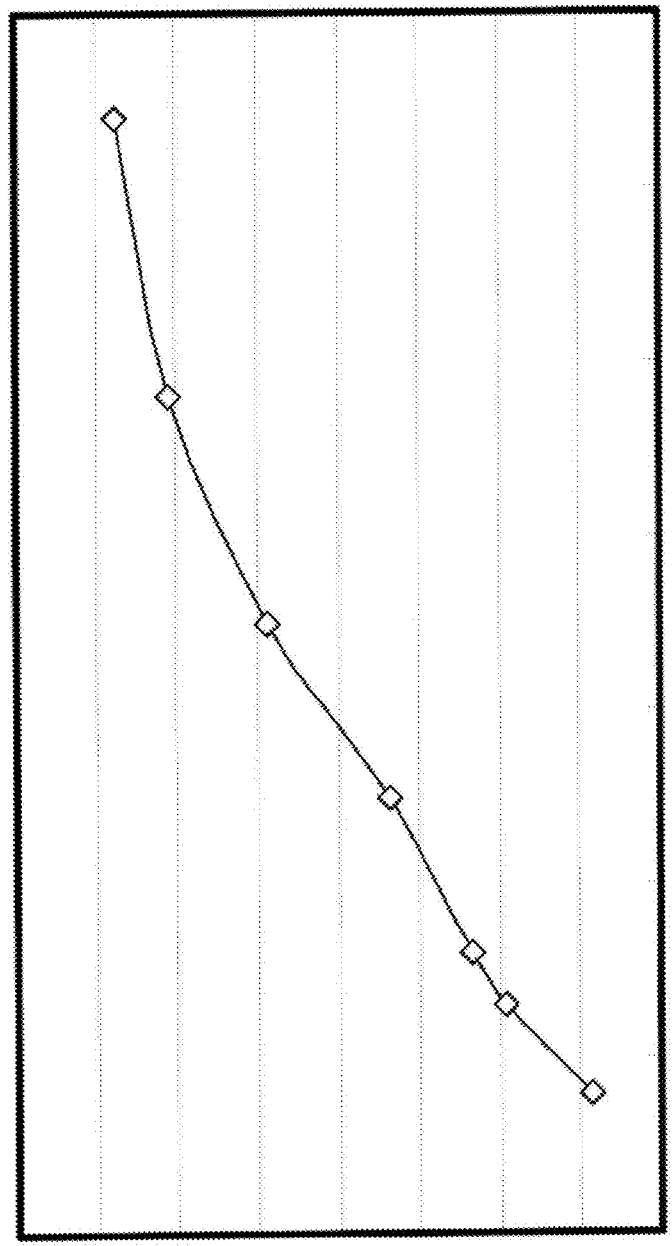
FIG. 12 is a graph illustrating the intensity of detected light from in the Example according to the present disclosure.

FIG. 12 is a graph showing examples of actual measurements of the changes in the intensity of light detected by the photodetecting body 12 when the light of a wavelength of 1904 nm is emitted from the light-emitting body 11 and the moist steam is heated under prescribed temperature and pressure conditions. The light of the 1904 nm wavelength is absorbed by two-molecule water molecules that have a single hydrogen bond, and thus the intensity of the light detected by the photodetecting body 12 increases as the absorption by the moist steam decreases as the moist steam is heated and the dryness fraction approaches 1 from 0. Consequently, there is a correlation between the dryness fraction of the moist steam within the pipe 21 and the intensity of light detected by the photodetecting body 12. In other words, there is a correlation between the dryness fraction of the moist steam within the pipe 21 and the amount of light absorbed by the moist steam.

Here, as illustrated in FIG. 4, while the boiling point of water is 100° at standard atmospheric pressure, it will vary depending on the pressure. Consequently, although, as described above, there is a correlation between the dryness fraction of the moist steam within the pipe 21 and the intensity of light that traverses the moist steam, the state of this correlation will vary depending on the temperature and pressure of the moist steam within the pipe 21.

An arbitrary temperature sensor or pressure sensor can be used in the environment sensor 13 illustrated in FIG. 1.

A central calculation processing device (CPU) 300 is connected to the photodetecting body 12 and the environment sensor 13. The dryness fraction identifying portion 301 is included in the CPU 300. A data memory device 400 that includes a relationship storing portion 401 is connected to the CPU 300. The relationship storing portion 401 stores, for each temperature and pressure condition, the relationship between the detected light intensity for each of the plurality of photodetecting elements 112a, 112b, 112c, and so forth, in the photodetecting body 12, acquired in advance, for example, and the dryness fraction of the moist steam. The relationship between the light reception intensity and the dryness fraction may be stored as an equation, or may be stored as a table.

The relationship between the respective detected light intensities for the plurality of photodetecting elements 112a, 112b, 112c, and so forth, included in the photodetecting body 12, to the dryness fraction of the moist steam can be acquired in advance through, for example, measuring the intensity of light that is transmitted through the moist steam together with measuring the dryness fraction of the moist steam using a conventional dryness fraction gauge while heating the moist steam using a boiler, or the like. While conventionally there is a variety of dryness fraction gauges, these may be used singly or in combination when acquiring the relationships.

The dryness fraction identifying portion 301 receives, from each of the plurality of photodetecting elements 112a, 112b, 112c, and so forth, included in the photodetecting body 12, a measured value for the intensity of light that has traversed the moist steam within the pipe 21. Moreover, the dryness fraction identifying portion 301 receives the measured values for the temperature and pressure of the moist steam within the pipe 21 from the environment sensor 13. Moreover, the dryness fraction identifying portion 301 reads out, from the relationship storing portion 401, the relationship between the intensity light of detected by the photodetecting elements and that the dryness fractions of the moist steam under temperature and pressure conditions corresponding to the measured values for the temperature and pressure for the moist steam.

Here if the relationship under temperature and pressure conditions that match the measured values for temperature and pressure are stored in the relationship storing portion 401, the dryness fraction identifying portion 301 reads out, from the relationship storing portion 401, the relationship with the temperature and pressure conditions that match the measured values for temperature and pressure. Moreover, if, for example, there is no relationship stored in the relationship storing portion 401 for temperature and pressure conditions matching the measured values for temperature and pressure, for example, then the dryness fraction identifying portion 301 reads out, from the relationship storing portion 401, the relationship that under the temperature and pressure conditions that are nearest to the measured values for the temperature and pressure.

Figure 13:
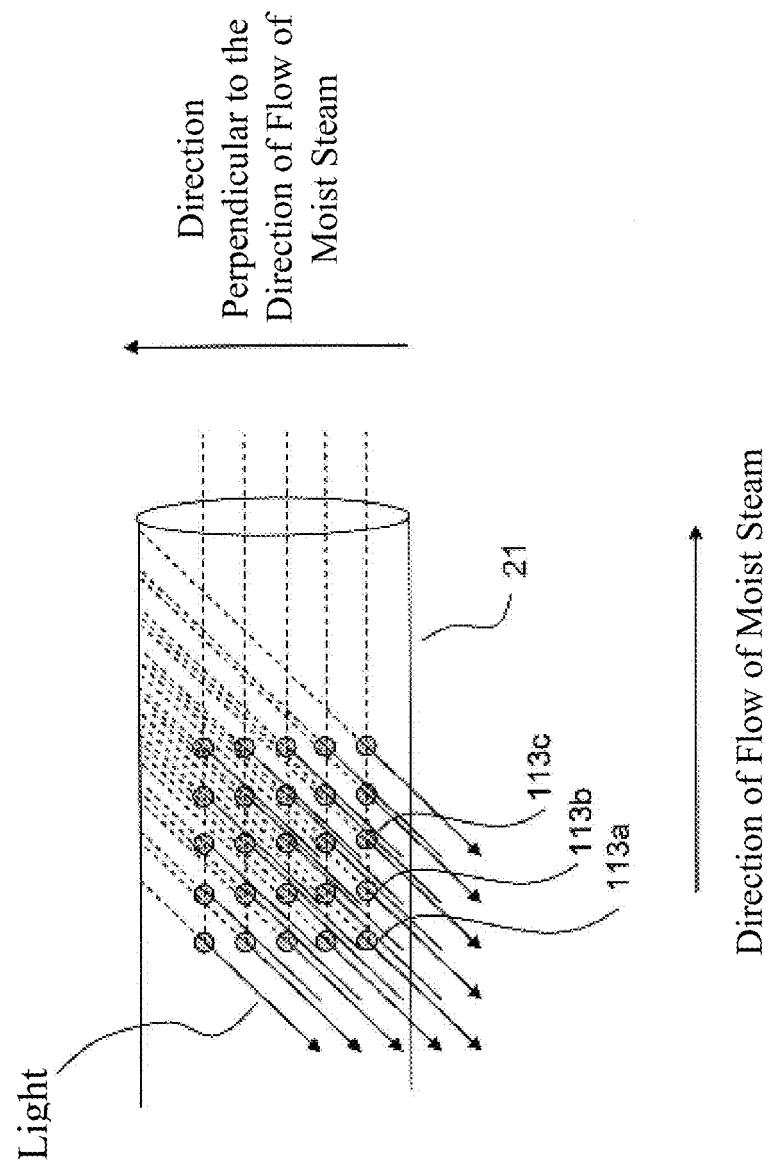
FIG. 13 is a schematic diagram illustrating positions within a pipe, corresponding to the respective positions of the plurality of photodetecting elements, in the Example according to the present disclosure.

The dryness fraction identifying portion 301 specifies the values of the dryness fractions for the moist steam at the positions before 113a, 113b, 113c, and so forth, in the pipe 21, as illustrated in FIG. 13, corresponding to the respective positions of the plurality of photodetecting elements 112a, 112b, 112c, and so forth, based on the measured values of the intensities of light detected by the respective plurality of photodetecting elements 112a, 112b, and 112c, and the relationships that have been read out. For example, when the relationship is expressed as an expression with the detected light intensity as the independent variable and the dryness fraction as the dependent variable, the dryness fraction identifying portion 301 substitutes the detected light intensity into the independent variable for the detected light intensity in the expression, to calculate the values for the dryness fractions for the moist steam at the positions corresponding respectively to the plurality of photodetecting elements 112a, 112b, 112c, and so forth, within the pipe 21.

Figure 14:
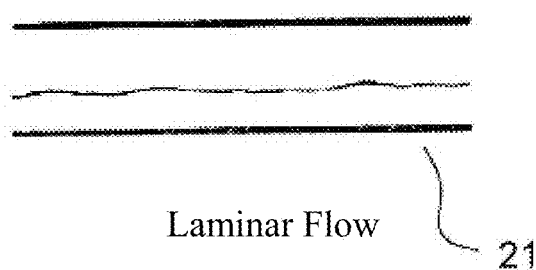
FIG. 14 is a schematic diagram illustrating laminar flow in the Example according to the present invention.
Figure 15:
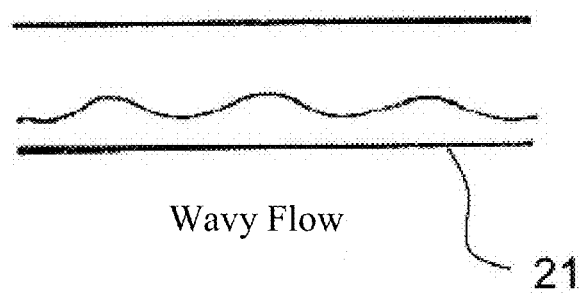
FIG. 15 is a schematic diagram illustrating waveform flow in the Example according to the present invention.
Figure 16:
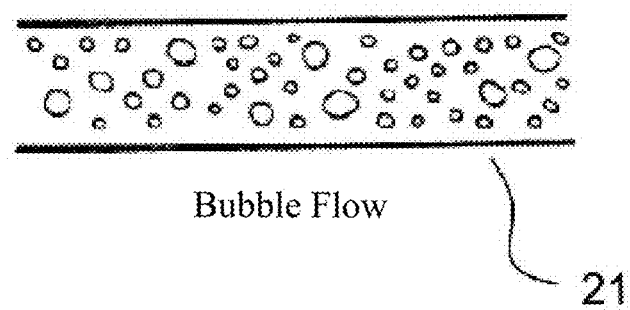
FIG. 16 is a schematic diagram illustrating gas bubble flow in the Example according to the present invention.
Figure 17:
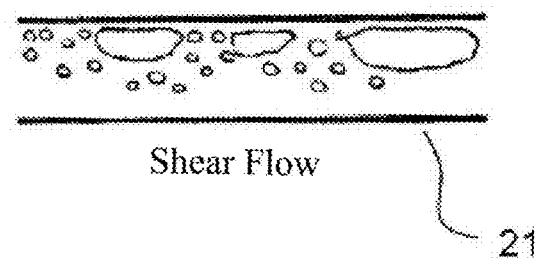
FIG. 17 is a schematic diagram illustrating laminar flow in the Example according to the present invention.
Figure 19:
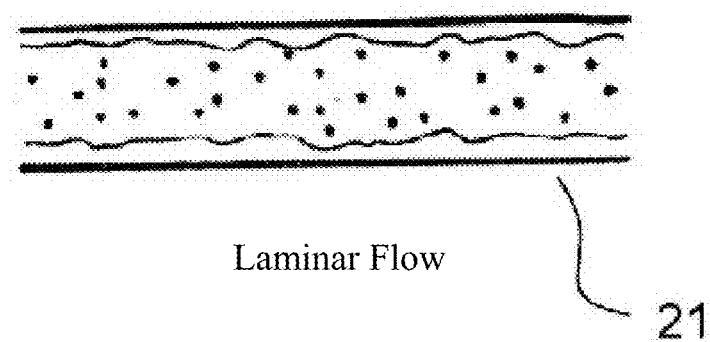
FIG. 19 is a schematic diagram illustrating annular flow in the Example according to the present invention.
Figure 20:
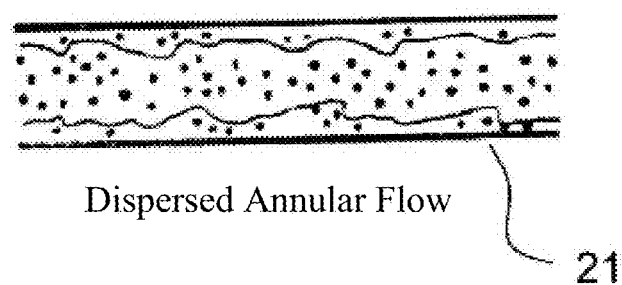
FIG. 20 is a schematic diagram illustrating dispersed annular flow in the Example according to the present invention.

There are various types of fluid flows for the two-phase flow that flows in the pipe 21 to produce the distribution of dryness fractions within the pipe 21. For example, in a state wherein the average dryness fraction within the pipe 21 is low, the type of fluid flow for the two-phase flow will be a laminar flow, as illustrated in FIG. 14, or the wavy flow as illustrated in FIG. 15, but when the average dryness fraction is increased, it will be the bubble flow that is illustrated in FIG. 16 or the sheer flow that is illustrated in FIG. 17, and when the average dryness fraction is increased further, it will be the slug flow as illustrated in FIG. 18, and when the average dryness fraction is increased even further, then it will be the annular flow as illustrated in FIG. 19 or the dispersed annular flow as illustrated in FIG. 20.

Figure 18:
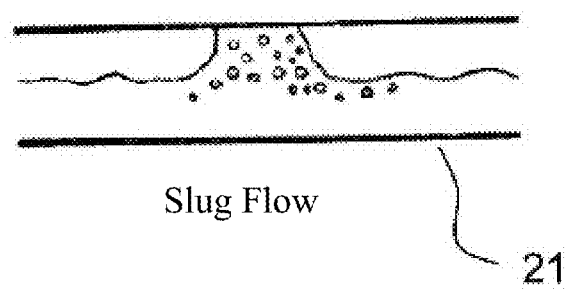
FIG. 18 is a schematic diagram illustrating slug flow in the Example according to the present invention.

Here in the slug flow that is illustrated in FIG. 18, for example, the average dryness fraction within the pipe 21 is low, but large bubbles are produced within the pipe 21. Given this, the dryness fraction will be locally high within the bubble parts, and the dryness fraction will be locally low in the other liquid parts. Consequently, if the dryness fraction of only a bubble part in the slug flow were to be measured locally, then an incorrect conclusion that the average dryness fraction within the pipe is high would the drawn. Such a case may make it impossible to perform the desired heat exchange within a heat exchanger, for example.

In contrast, the dryness fraction distribution measuring device according to the Example makes it possible to measure the distribution of the dryness fraction in the moist steam within the pipe 21. Because of this, it is possible to evaluate whether the type of fluid flow in the two-phase flow within the pipe 21 is laminar flow, wavy flow, sheer flow, slug flow, annular flow, bubble flow, or annular spray flow.

As illustrated in FIG. 1, the CPU 300 is further provided with an image generating portion 302 for generating an image that shows the dryness fractions of the moist steam in positions corresponding to each of the plurality of photodetecting elements. If, for example, measurements of the detected light intensity, indicating the dryness fractions, are carried out in the five points along the direction of flow of the moist steam and five points in the direction that is perpendicular to the direction of flow of the moist steam, then the image generating portion 302 would create, as an image of the detected light intensity or the amount of light absorbed at each of the individual management positions, a table showing the dryness fractions of the moist steam at positions corresponding to the plurality of photodetecting elements, as illustrated in FIG. 21.

Figure 22:
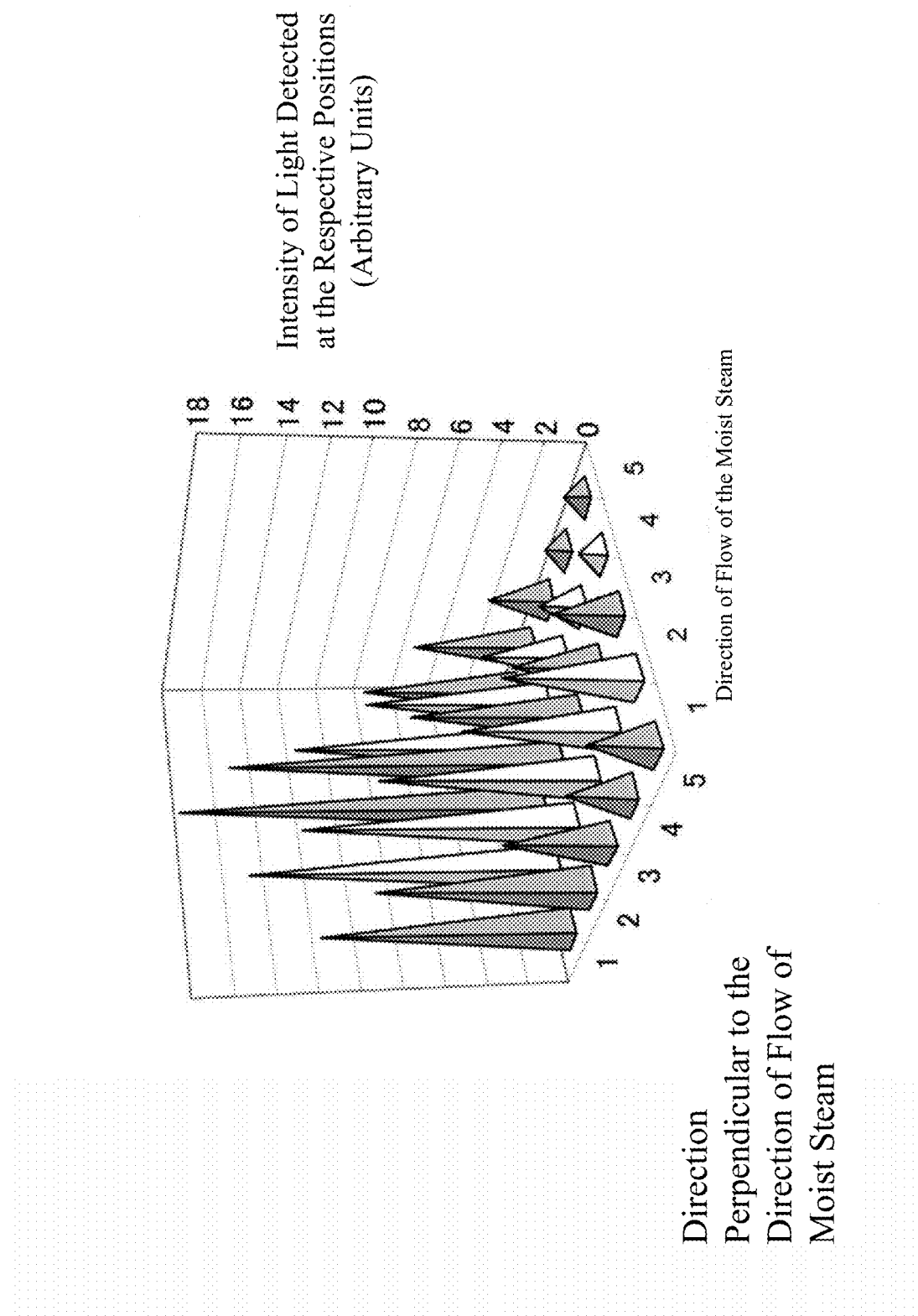
FIG. 22 is a bar graph of the light reception intensities in respective measurement locations in the Example according to the present invention.
Figure 23:
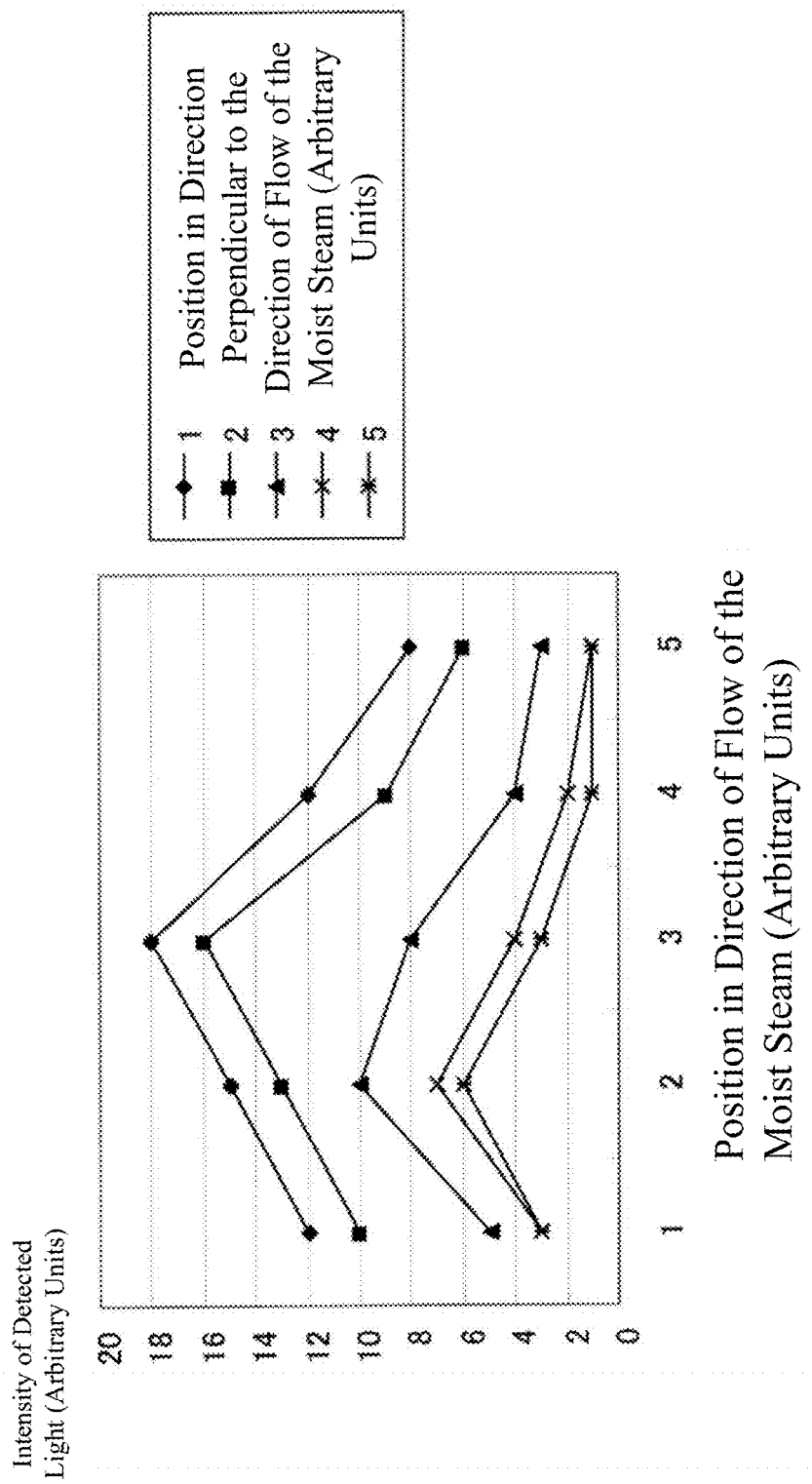
FIG. 23 is a line graph of the light reception intensities in respective measurement locations in the Example according to the present invention.
Figure 24:
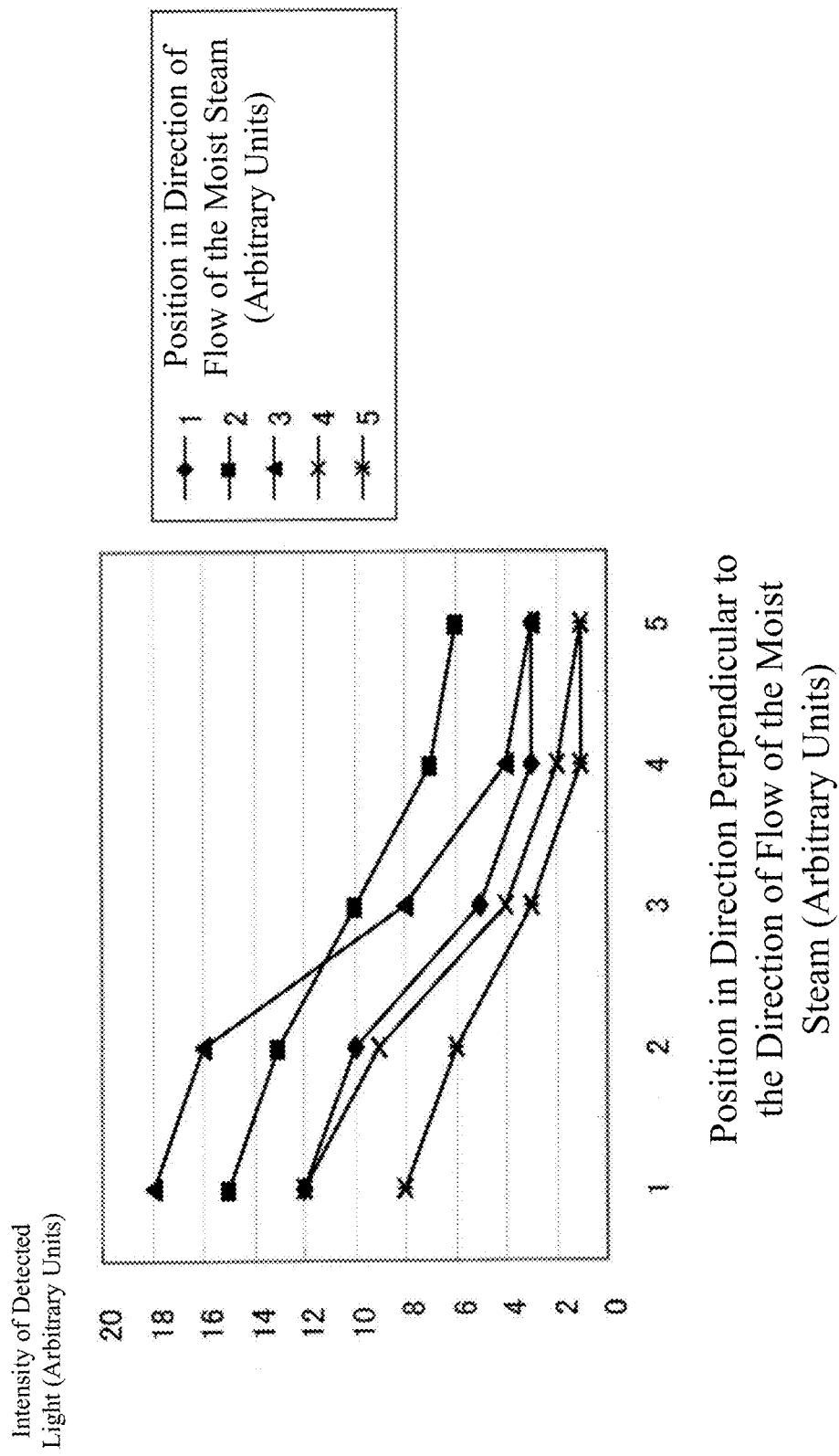
FIG. 24 is a line graph of the light reception intensities in respective measurement locations in the Example according to the present invention.

Conversely, the image generating portion 302 may generate a bar graph of the detected light intensities for of the amount of light absorption at each of the individual measurement positions, as illustrated in FIG. 22, as an image showing the dryness fractions of the moist steam at the respective positions corresponding to the plurality of photodetecting elements. Conversely, the image generating portion 302 may make a line graph plotting the detected light intensities or the amounts of light absorbed at positions in the direction of flow of the moist steam, as illustrated in FIG. 23, as an image showing the dryness fractions of the moist steam at respective positions corresponding to the plurality of photodetecting elements, or, as illustrated in FIG. 24, may make a line graph plotting the detected light intensities or amounts of light absorbed at positions in directions perpendicular to the direction of flow of the moist steam, as an image showing the dryness fractions of the moist steam at respective positions corresponding to the plurality of photodetecting elements.

Figure 26:
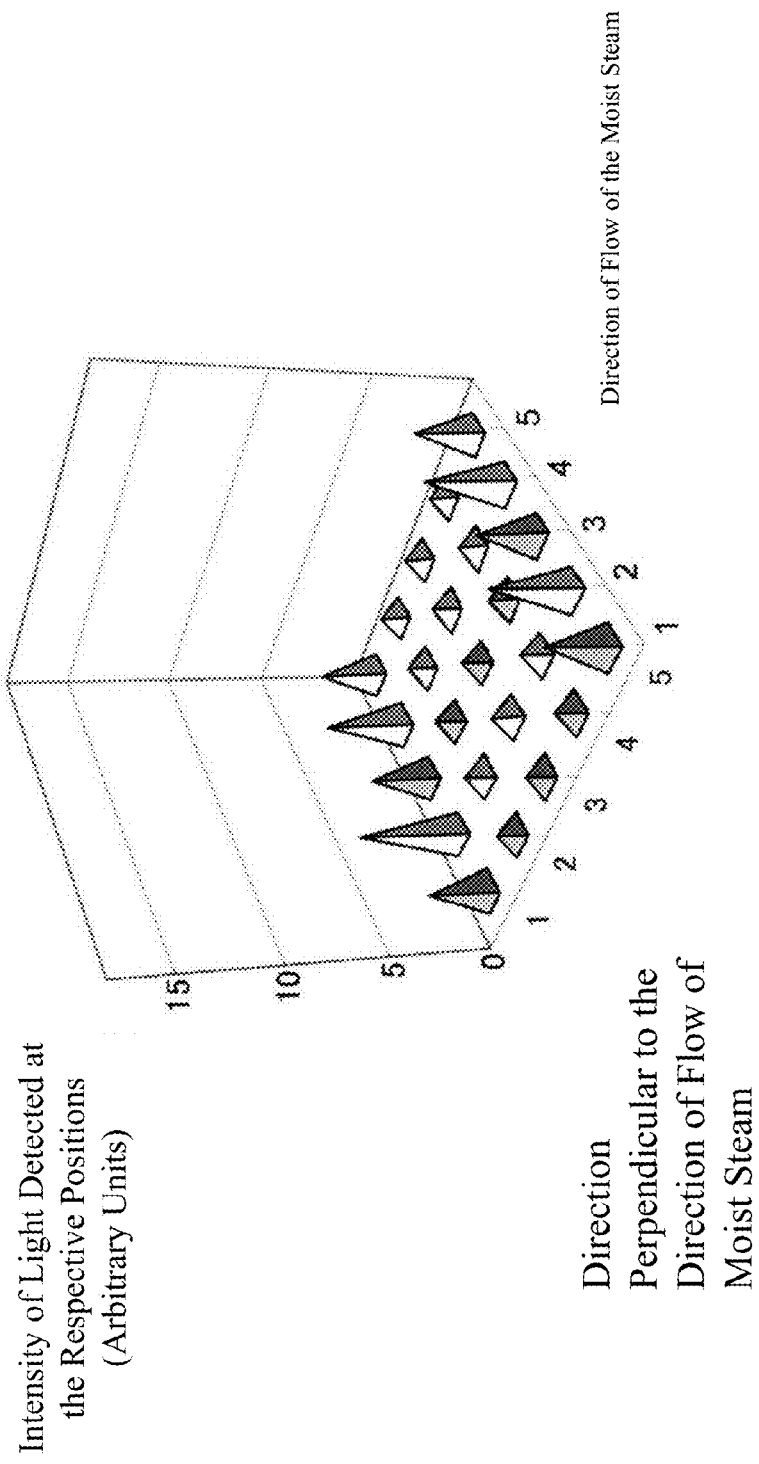
FIG. 26 is a bar graph of the light reception intensities in respective measurement locations in the Example according to the present invention.
Figure 27:
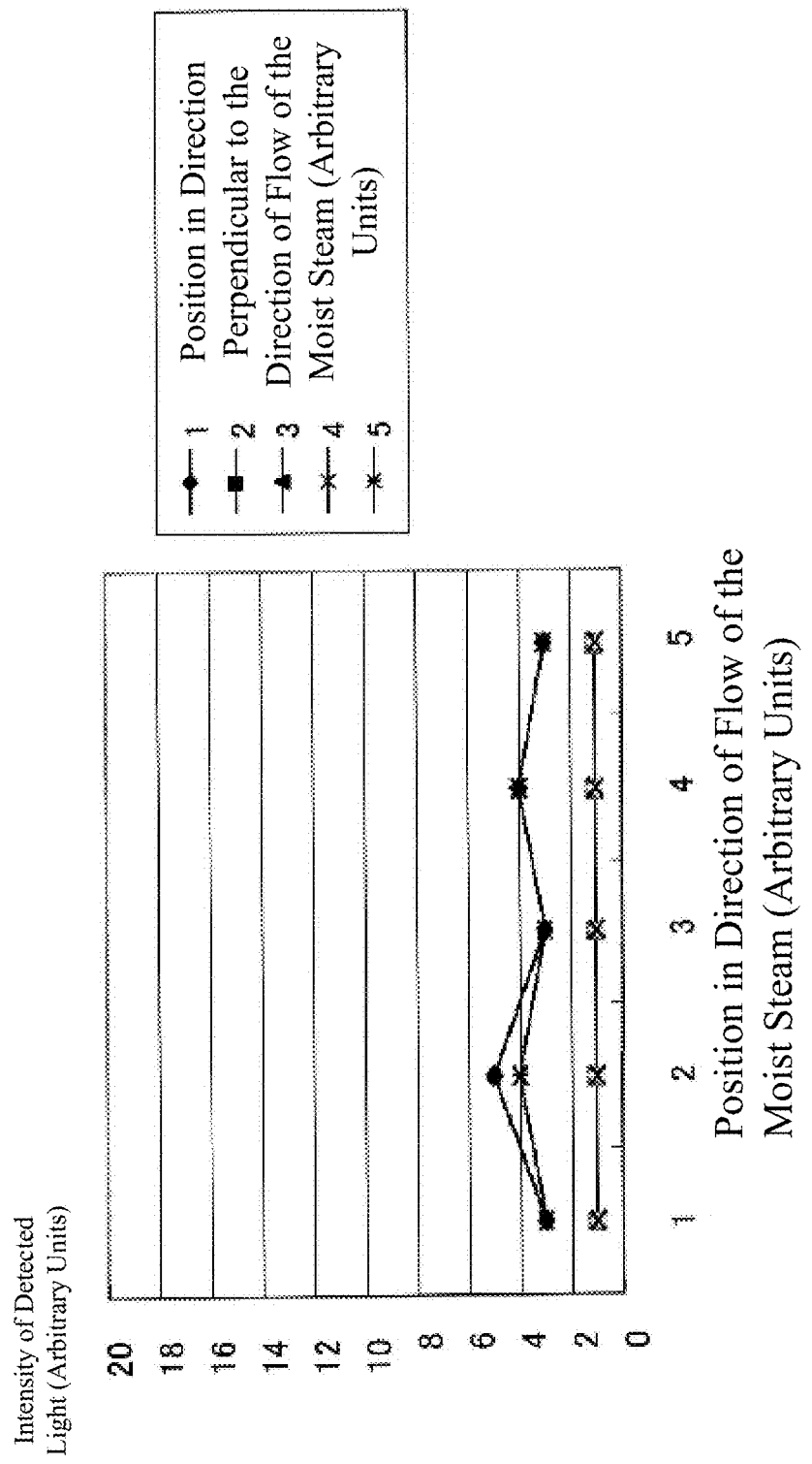
FIG. 27 is a line graph of the light reception intensities in respective measurement locations in the Example according to the present invention.
Figure 28:
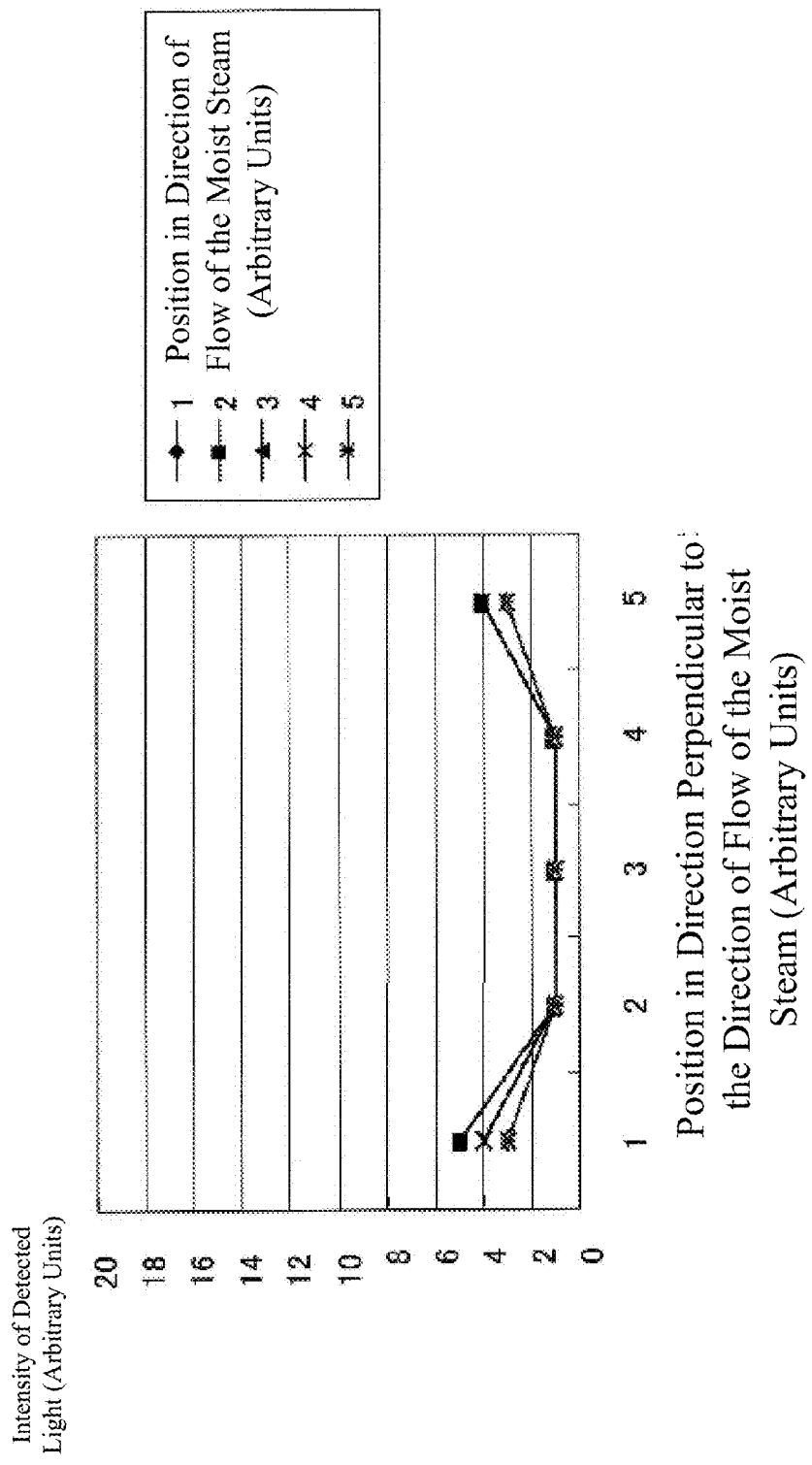
FIG. 28 is a line graph of the light reception intensities in respective measurement locations in the Example according to the present invention.

Note that FIG. 21 through FIG. 24 are examples for the case wherein the form of fluid flow of the moist steam within the pipe 21 is slug flow, examples wherein there is a great amount of variability in the detected light intensities that indicate the dryness fractions. In contrast, in the case of the form of fluid flow of the moist steam in the pipe 21 being, for example, annular flow, the amount of variability in the detected light intensity, which indicates the dryness fractions, will be small, with a table as illustrated in FIG. 25, for example, a bar graph as illustrated in FIG. 26, for example, and line graphs as illustrated in FIG. 27 and FIG. 28, for example.

Moreover, the dryness fraction distribution measuring device as set forth in the Example, as illustrated in FIG. 1, further includes: an evaluating portion 303 for evaluating whether or not the non-uniformity in the dryness fractions for the moist steam at the respective positions corresponding to the plurality of photodetecting elements is at or greater than a prescribed upper limit reference value or for evaluating whether or not the non-uniformity is at or less than a prescribed lower limit reference value; and a heating device 41 for heating the moist steam if the non-uniformity in the dryness fractions of the moist steam is at or above the prescribed upper limit reference value, and for stopping heating of the moist steam if the non-uniformity in the dryness fractions of the moist steam is at or below the prescribed lower limit reference value. The evaluating portion 303 is included in the CPU 300. The heating device 41 is connected electrically to the evaluating portion 303 that is included in the CPU 300. The prescribed upper limit reference value and lower limit reference value for the non-uniformity and the dryness fractions for the moist steam are stored in a reference storing portion 402 in the data storing device 400.

The evaluating portion 303 calculates, as a value indicating the non-uniformity of the dryness fractions, the scatter, or the like, in values of the dryness fractions for the moist steam in the respective positions corresponding to the plurality of photodetecting elements identified by the dryness fraction identifying portion 301. Furthermore, the evaluating portion 303 reads out the prescribed upper limit reference value from the reference storing portion 402, and compares the scatter in the calculated values for the dryness fraction to the upper limit reference value. If the scatter in the calculated values for the dryness fractions is greater than the upper limit reference value, then the evaluating portion 303 evaluates that it is necessary to heat the moist steam.

Note that in the annular flow, illustrated in FIG. 19, or the dispersed annular flow, illustrated in FIG. 20, the non-uniformity in the dryness fraction is low, and in the laminar flow, illustrated in FIG. 14, the wavy flow, illustrated in FIG. 15, the bubble flow, illustrated in FIG. 16, the sheer flow, illustrated in FIG. 17, and the slug flow, illustrated in FIG. 18, the non-uniformity in the dryness fractions is large. When heating an object such as a heat exchanger, or the like, the use of moist steam wherein the non-uniformity in the dryness fractions is low, such as with annular flow or annular spray flow, is preferred due to the efficiency of thermal conduction. Consequently, the prescribed upper limit reference value that is stored in the reference storing portion 402, for example, is set so that if the non-uniformity in the dryness fractions is less than the upper limit reference value, then the moist steam will have an annular flow or an annular spray flow.

Moreover, with an annular flow or an annular spray flow, the variability in the dryness fraction will be low in the direction of flow of the moist steam, as illustrated in FIG. 27, and, as illustrated in FIG. 28, in the direction that is perpendicular to the direction of flow of the moist steam, there will be a tendency for the dryness fraction be low in the center of the pipe 21 with the dryness fractions higher in the vicinities of the side walls of the pipe 21. Because of this, the evaluating portion 303 may evaluate whether or not it is necessary to heat the moist steam, based on the distribution of the dryness fractions in the direction of flow of the moist steam and based on symmetry of the dryness fractions in respect to the center of the pipe 21 in the direction perpendicular to the direction of flow of the moist steam.

Furthermore, when there is a concern regarding drying out due to overheating of an object such as a heat exchanger, or the like, then the prescribed lower limit reference value that is stored in the reference storing portion 402 that is illustrated in FIG. 1, for example, is set so that insofar as the non-uniformity in the dryness fraction is greater than the lower limit reference value the moist steam will include enough mist to avoid drying out.

The heating device 41 heats the moist steam that is flowing in the pipe 21, through heating, for example, the pipe 21, when the evaluating portion 303 evaluates that it is necessary to heat the moist theme. Moreover, the heating of the moist steam is stopped if the evaluating portion 303 evaluates that the non-uniformity in the dryness fraction of the moist steam is at or below the prescribed lower limit reference value.

Moreover, an inputting device 321, an outputting device 322, a program memory device 323, and a temporary memory device 324 are connected to the CPU 300. A switch, keyboard, or the like, may be used as the inputting device 321. The relationship between the detected light intensity for each temperature and pressure conditions and the dryness fraction that is stored in the relationship storing portion 401 is inputted using, for example, the inputting device 321. An optical indicator, a digital indicator, a liquid crystal display device, or the like, may be used as the outputting device 322. The outputting device 322 displays, for example, the distribution of dryness fractions in the moist steam at the respective positions corresponding to the plurality of photodetecting elements 112a, 112b, 112c, and so forth, within the pipe 21, specified by the dryness fraction identifying portion 301. Conversely, the outputting device 322 may output an image generated by the image generating portion 302. The program memory device 323 stores a program for executing, on the CPU 300, exchange of data between the devices that are connected to the CPU 300. The temporary memory device 324 stores data temporarily during the calculation processes of the CPU 300.

The dryness fraction distribution measuring device according to the example set forth above and the dryness fraction distribution measuring method that uses the dryness fraction distribution measuring device enable high accuracy measurements of moist steam dryness fractions at high speeds, using an optical method, rather than changing the phase state of the moist steam. Moreover, the dryness fraction distribution calculating device according to the Example does not require the provision of constriction valves or branched pipes within the pipes. Because of this, the dryness fraction distribution measuring device according to the Example can be installed at a low cost in the vicinity of that which is subject to heating, such as a heat exchanger.

Moreover, while conventionally there are dryness fraction meters that use ultrasound, with ultrasound there is a large difference in acoustic impedance at the boundary between the gas phase part and the liquid phase part of the moist steam, and thus it is mostly reflected at this boundary. Because of this, in a dryness fraction gauge that uses ultrasound, the ultrasound does not penetrate to the level wherein the dryness fraction can be measured practically. In contrast, light is able to traverse the boundary between the gas phase part and the liquid phase part. Because of this, the dryness fraction distribution measuring device according to the Example can measure the dryness fraction with high accuracy.

Note that the relationship storing portion 401 may store the relationship between the amount of light absorbed by the moist steam and the dryness fraction of the moist steam. In this case, the dryness fraction identifying portion 301 may calculate measured values for the amounts of light absorbed by the moist steam that is being measured, from the intensities of light emitted by the light emitting body 11 and the intensities of light detected by the photodetecting body 12, to identify the dryness fractions of the moist steam that is being measured, based on the relationship between the amount of light absorbed and the dryness fractions and on the measured values for the amounts of light absorbed.

Moreover, the state of correlation between the dryness fractions of the moist steam within the pipe 21 and the intensity of light traversing the moist steam may change depending also on the volume through which the light is transmitted. For example, factors that change the volume through which the light is transmitted include the diameter of the pipe, the area of the light-emitting body, the area of the photodetecting element, and the like. Consequently, the relationship storing portion 401 may store, for each volume of moist steam through which the light is transmitted, the correlation between the dryness fraction of the moist steam and the intensity of light that traverses the moist steam. In this case, the dryness fraction identifying portion 301 may read out, from the relationship storing portion 401, the relationship between the intensity of detected light and the dryness fraction corresponding to the values measured for the temperature and pressure of the moist steam and the values of the volume of moist steam that are subject to measurement, through which the light is transmitted.

Another Example

The Example showed an example where in the light-emitting body 11, illustrated in FIG. 1, emitted light having a single wavelength. In contrast, in Another Example, the light-emitting body 11 produces light at at least two different wavelengths. For example, one of these at least two different wavelengths is the 1880 nm wherein the absorption peak for water molecules appears when the number of hydrogen bonds is zero, and the other wavelength is the 1910 nm wherein the absorption peak of water molecules appears when the number of hydrogen bonds is 1. In this way, in the Another Example, the light that is produced by the light-emitting body 11 is set so that the degrees of optical absorption of each of the plurality of wavelengths is correlated to the number of hydrogen bonds that are formed between the water molecules in the cluster.

The light-emitting body 11 may be provided with a plurality of light-emitting elements for imaging respective lights of different colors. Conversely, the light-emitting body may emit light of a broad wavelength band. Moreover, a light-emitting diode, a super-luminescent diode, a semiconductor laser, a laser resonator, or the like, may be used for the light-emitting body 11. In the case wherein the light-emitting body 11 emits light of a broad wavelength band, a filter that transmits only at least two different wavelengths may be disposed in front of the photodetecting body 12. A photodiode, or the like, may be used for each of the photodetecting elements that are included in the photodetecting body 12. For example, each of the photodetecting elements that are included in the photodetecting body 12 receive, at least, the 1880 nm light that is most absorbed by the water molecules when the number of hydrogen bonds is 0, and the 1910 nm light that is most absorbed by the water molecules when the number of hydrogen bonds is 1.

Figure 29:
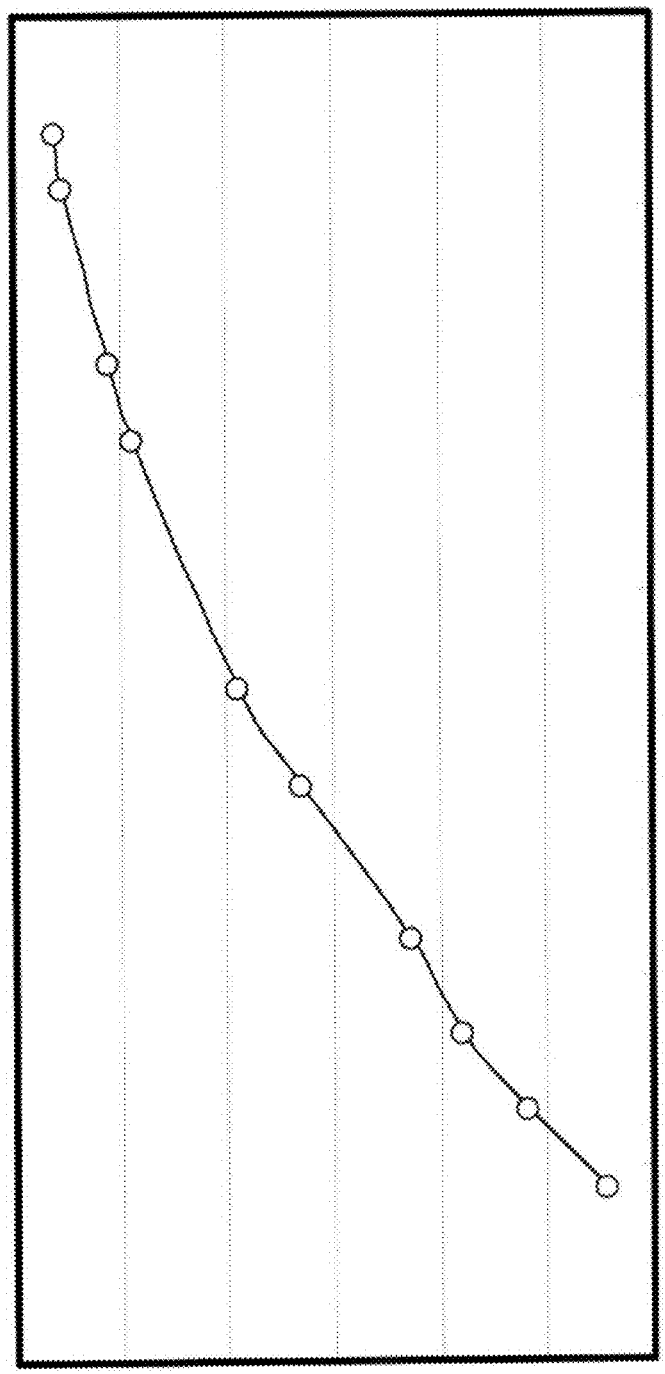
FIG. 29 is a graph illustrating the ratio of vapor calorific value and optical absorption according to Another Example according to the present disclosure.

FIG. 29 is a graph wherein actual measured examples for the ratio R, obtained by Equation (1), are plotted against the added heat of the moist steam, when I1 is the optical absorption of light at a wavelength of 1880 nm, and I2 is the optical absorption of light at a wavelength of 1910 nm, under specific temperature and pressure conditions.

$$R = I1/I2 \quad (1)$$

The light absorption ratio R is correlated to the ratio of water molecules existing singly, wherein no hydrogen bonds are formed, relative to clusters of water molecules wherein two water molecules are bonded together by one hydrogen bond. As described above, the average number of hydrogen bonds in a cluster falls as the dryness fraction moves from 0 to 1, where there tends to be an increase in the water molecules that exist singly. Consequently, the optical absorption ratio R tends to get larger as the dryness fraction approaches 1 from 0 as wet steam is heated.

Note that a similar result is produced even when plotting the ratio R, produced through Equation (2), below, versus the amount of seating of the moist steam, with the amount of light absorption of light with a wavelength of 1760 nm defined as a I0:

$$R = (I1 - I0)/(I2 - I0) \quad (2)$$

Here the I0, which is the amount of absorption of light with a wavelength of 1760 nm, is the part that is unrelated to absorption of light by water molecules, but has an effect on the amount of the absorption spectrum that is captured. Consequently, in Equation (2), taking the difference between the I1 and the I0, and between the I2 and the I0 makes it possible to produce a constant baseline for the spectroscopic spectrum.

In the Another Example, the relationship storing portion 401 stores, for example, relationships obtained in advance between the light absorption ratios R expressed in Equation (1) and Equation (2) and the dryness fraction for each temperature and pressure condition. The relationship between the light absorption ratio R and the dryness fraction may be stored as an equation, or may be stored as a table.

In the Another Example, the dryness fraction identifying portion 301 calculates the dryness fraction of the moist steam based on a plurality of magnitude relationships between measured values of intensities of light that has traversed the moist steam at the respective plurality of wavelengths. For example, the dryness fraction identifying portion 301 receives, from each of the photodetecting elements included in the photodetecting body 12, an intensity spectrum for light that has traversed the moist steam within the pipe 21. Furthermore, the dryness fraction identifying portion 301 calculates the optical absorption spectrum due to the moist steam based on the optical intensity spectrum of the light prior to traversing the moist steam within the pipe 21 and the optical intensity spectrum of the light that has traversed the moist steam within the pipe 21. Moreover, the dryness fraction identifying portion 301 calculates the optical absorption ratio R as expressed by the aforementioned Equations (1) and (2) based on the absorption spectrum.

Moreover, the dryness fraction identifying portion 301 reads out, from the relationship storing portion 401, the relationship between the light absorbing ratio R and the dryness fraction, under temperature and pressure conditions corresponding to the measured values for temperature and pressure of the moist steam. The dryness fraction identifying portion 301 calculates the value for the moist steam within the pipe 21 based on the value for the light absorbing ratio R that has been calculated and on the relationship between the light absorbing ratio R and the dryness fraction.

The other structural elements in the dryness factor distribution measuring device according to the Another Example are identical to those in the Example. The dryness factor distribution measuring device according to the Another Example, through the use of light of a plurality of wavelengths, enables suppression of variability in the outputs of the light-emitting body 11 and suppression of the influence of noise. Because of this, this makes it possible to identify more accurately the values for the dryness fractions of the moist steam that is subject to measurement.

Alternate Form of the Another Example

An example of comparing the degree of absorption at the 1880 nm wavelength and the degree of absorption at the 1910 nm wavelength was described in the Another Example. Here the numerator and the denominator on the right-hand side of Equations (1) and (2) may be switched. Moreover, the optical absorption of the wavelength corresponding to the number of hydrogen bonds being zero and the optical absorption of the wavelength corresponding to the number of hydrogen bonds being two may be compared. Conversely, the optical absorption of the wavelength corresponding to the number of hydrogen bonds being zero and the optical absorption of the wavelength corresponding to the number of hydrogen bonds being three may be compared. Moreover, the optical absorption of the wavelength that is correlated to the number of hydrogen bonds being one and the optical absorption of the wavelength that is correlated to the number of hydrogen bonds being two may be compared, the optical absorption of the wavelength that is correlated to the number of hydrogen bonds being one and the optical absorption of the wavelength that is correlated to the number of hydrogen bonds being three may be compared, and the optical absorption of the wavelength that is correlated to the number of hydrogen bonds being two and the optical absorption of the wavelength that is correlated to the number of hydrogen bonds being three may be compared. In this way, the dryness fraction may be calculated based on the ratios of optical absorption means of an arbitrary plurality of wavelengths that are correlated to different numbers of hydrogen bonds. Conversely, a correlation may be established in advance between the dryness fraction and the differences between optical absorption means of an arbitrary plurality of wavelengths that are correlated to different numbers of hydrogen bonds, and the value for the dryness fraction may be calculated from the measured values for the differences between the optical absorptions of the plurality of wavelengths.

Yet Another Example

Figure 30:
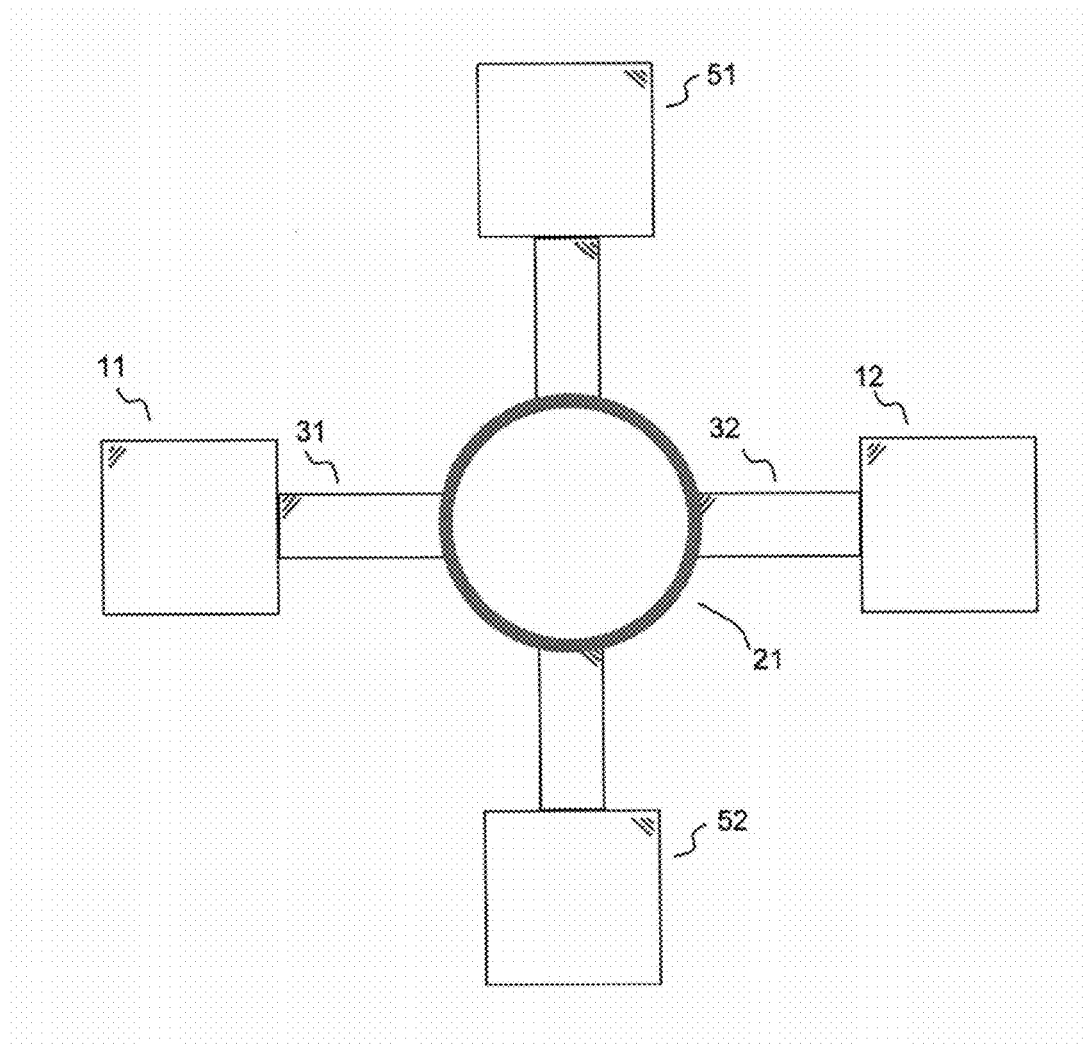
FIG. 30 is a schematic diagram of a dryness fraction distribution measuring device as set forth in Yet Another Example according to the present disclosure.

The Example and Another Example illustrated examples wherein the dryness fraction distribution measuring device had one set of a light-emitting body 11 and a photodetecting body 12, as illustrated in FIG. 1. In contrast, the dryness fraction distribution measuring device may have, in addition to the combination of the light-emitting body 11 and the photodetecting body 12, a combination of a light-emitting body 51 and a photodetecting body 52, as illustrated in FIG. 30. For example, the combination of the light-emitting body 51 and the photodetecting body 52 may be disposed in a direction that is perpendicular to that of the combination of the light-emitting body 11 and the photodetecting body 12. Doing so makes it possible to measure the distribution of dryness fractions spatially within the pipe 21 based on the intensities of detected light measured at the respective photodetecting elements included in the photodetecting body 12 and the intensities of detected light measured by the respective photodetecting elements included in the photodetecting body 52.

Other Examples

While there are descriptions of examples as set forth above, the descriptions and drawings that form a portion of the disclosure are not to be understood to limit the present disclosure. A variety of alternate examples and operating technologies should be obvious to those skilled in the art. For example, the gas/liquid two-phase flow may be that of a coolant, rather than being limited to water vapor. Moreover, while in FIG. 1 the light-emitting body 11 and the photodetecting body 12 face each other, the light-emitting body and the photodetecting body may be integrated together instead. In this case, a reflecting plate is disposed on the side wall of the pipe that faces the integrated light-emitting body and photodetecting body. The light that is produced by the integrated light-emitting body and photodetecting body passes through the interior of the pipe and is reflected by the reflecting plate, to be detected by the integrated light-emitting body and photodetecting body. Moreover, the principle for measuring the dryness fractions in the invention according to the present application is not limited to the theory explained in the examples. Instead, the differences in the absorption spectra between, for example, saturated vapor and saturated liquid may be explained in terms of differences between the resonant energies between the respective water molecules. However, whichever the case, there is no difference in the point that it is possible to measure the dryness fraction based on the intensity of light that passes through the moist steam. In this way, the present disclosure should be understood to include a variety of examples, and the like, not set forth herein.

The dryness fraction distribution measuring device according to the examples according to the present disclosure can be used in exposing the effects of increasing latent heat through a decompression valve, used in dryness fraction measurements for producing optimal boiler efficiency, used in steam turbine moisture loss measurements, used in optimal dryness fraction control of heat exchanging equipment, used in control of foodstuff manufacturing processes, such as in pasta making, used in the control of chemical processes, and the like.

The invention claimed is:

1. A dryness fraction distribution measuring device, comprising:
a light-emitting body that illuminates a gas/liquid two-phase flow with light;
an environment sensor that measures at least one of temperature or pressure in the gas/liquid two-phase flow;
a plurality of photodetecting elements that receive respective lights that have traversed moist steam;
a relationship storing portion that stores, for each temperature or pressure, a relationship between an intensity of light that has traversed the gas/liquid two-phase flow and a dryness fraction of the gas/liquid two-phase flow; and
a dryness fraction identifying portion that identifies a dryness fraction of the gas/liquid two-phase flow for each position corresponding to the plurality of photodetecting elements, based on the relationships between the measured values for the detected light intensities of the lights detected by the respective photodetecting elements and the values for the at least one of temperatures or pressures measured by the environment sensor.

2. The dryness fraction distribution measuring device as set forth in claim 1, further comprising:
a heating device that heats the gas/liquid two-phase flow if the non-uniformity in the dryness fractions in the gas/liquid two-phase flow at respective positions corresponding to the plurality of photodetecting elements is equal to or greater than a prescribed reference.

3. The dryness fraction distribution measuring device as set forth in claim 1, further comprising:
an image generating portion that generates an image showing dryness fractions of the gas/liquid two-phase flow at respective positions corresponding to the plurality of photodetecting elements.

4. The dryness fraction distribution measuring device as set forth in claim 1, wherein:
the plurality of photodetecting elements are arranged along the direction of flow of the gas/liquid two-phase flow.

5. The dryness fraction distribution measuring device as set forth in claim 1, wherein:
the plurality of photodetecting elements are arranged perpendicularly to the direction of flow of the gas/liquid two-phase flow.

6. The dryness fraction distribution measuring device as set forth in claim 1, wherein:
the plurality of photodetecting elements is arranged in two dimensions, along the direction of the flow of the gas/liquid two-phase flow and along the direction that is perpendicular to the direction of flow of the gas/liquid two-phase flow.

7. The dryness fraction distribution measuring device as set forth in claim 1, wherein:
the amount of absorption of light in the gas/liquid two-phase flow is correlated with the number of hydrogen bonds, or the presence/absence thereof, that are formed in the gas/liquid two-phase flow.

8. The dryness fraction distribution measuring device as set forth claim 1, wherein:
the light-emitting body illuminates the gas/liquid two-phase flow with light of a plurality of wavelengths.

9. The dryness fraction distribution measuring device as set forth in claim 8, wherein:
the amounts of absorption of respective lights in the plurality of wavelengths are correlated to the number of hydrogen bonds, or the presence/absence thereof, formed in the gas/liquid two-phase flow.

10. A dryness fraction distribution measuring method, comprising:
illumination of a gas/liquid two-phase flow with light;
reception of light, which has traversed the gas/liquid two-phase flow, by a respective photodetecting elements;
measuring at least one of temperature or pressure in the gas/liquid two-phase flow;
preparation of a relationship between an intensity of light that has traversed the gas/liquid two-phase flow and a dryness fraction of the gas/liquid two-phase flow, obtained in advance for individual temperatures and pressures; and
identification of a dryness fraction of the gas/liquid two-phase flow for each position corresponding to the plurality of photodetecting elements, based on the relationships between the measured values for the detected light intensities of the lights detected by the respective photodetecting elements and measured values for the at least one temperatures or pressures.

11. The dryness fraction distribution measuring method as set forth in claim 10, further comprising:
heating the gas/liquid two-phase flow if the non-uniformity in the dryness fractions in the gas/liquid two-phase flow at respective positions corresponding to the plurality of photodetecting elements is equal to or greater than a prescribed reference.

12. The dryness fraction distribution measuring method as set forth in claim 10, further comprising:
generating an image showing dryness fractions of the gas/liquid two-phase flow at respective positions corresponding to the plurality of photodetecting elements.

13. The dryness fraction distribution measuring method as set forth in claim 10, wherein:
the plurality of photodetecting elements are arranged along the direction of flow of the gas/liquid two-phase flow.

14. The dryness fraction distribution measuring method as set forth in claim 10, wherein:
the plurality of photodetecting elements are arranged perpendicularly to the direction of flow of the gas/liquid two-phase flow.

15. The dryness fraction distribution measuring method as set forth in claim 10, wherein:
the plurality of photodetecting elements is arranged in two dimensions, along the direction of the flow of the gas/liquid two-phase flow and along the direction that is perpendicular to the direction of flow of the gas/liquid two-phase flow.

16. The dryness fraction distribution measuring method as set forth in claim 10, wherein:
the amount of absorption of light in the gas/liquid two-phase flow is correlated with the number of hydrogen bonds, or the presence/absence thereof, that are formed in the gas/liquid two-phase flow.

17. The dryness fraction distribution measuring method as set forth in claim 10, wherein:
in the illumination with light, light of a plurality of wavelengths is emitted.

18. The dryness fraction distribution measuring method as set forth in claim 17, further comprising:
the amounts of absorption of respective lights in the plurality of wavelengths are correlated to the number of hydrogen bonds, or the presence/absence thereof, formed in the gas/liquid two-phase flow.

\* \* \* \* \*